(12) United States Patent
Suzuki et al.

(10) Patent No.: US 11,672,911 B2
(45) Date of Patent: Jun. 13, 2023

(54) NEEDLELESS INJECTOR, METHOD OF ADJUSTING ON-COMPLETION REACHED DEPTH WITH NEEDLELESS INJECTOR, AND EJECTION PARAMETER CALCULATION PROGRAM FOR NEEDLELESS INJECTOR

(71) Applicant: DAICEL CORPORATION, Osaka (JP)

(72) Inventors: Takamasa Suzuki, Hyogo (JP); Shingo Atobe, Osaka (JP); Hiroshi Miyazaki, Osaka (JP); Hiromitsu Iga, Hyogo (JP); Katsuya Miki, Osaka (JP)

(73) Assignee: Daicel Corporation, Osaka (JP)

( * ) Notice: Subject to any disclaimer, the term of this patent is extended or adjusted under 35 U.S.C. 154(b) by 576 days.

(21) Appl. No.: 16/626,291

(22) PCT Filed: Jun. 27, 2018

(86) PCT No.: PCT/JP2018/024466
§ 371 (c)(1),
(2) Date: Dec. 23, 2019

(87) PCT Pub. No.: WO2019/004322
PCT Pub. Date: Jan. 3, 2019

(65) Prior Publication Data
US 2020/0276392 A1 Sep. 3, 2020

(30) Foreign Application Priority Data
Jun. 27, 2017 (JP) .............................. JP2017-125672

(51) Int. Cl.
*A61M 5/178* (2006.01)
*A61M 5/20* (2006.01)
*A61M 5/30* (2006.01)

(52) U.S. Cl.
CPC ........ *A61M 5/2046* (2013.01); *A61M 5/2053* (2013.01); *A61M 5/30* (2013.01);
(Continued)

(58) Field of Classification Search
CPC .... A61M 5/2046; A61M 5/2053; A61M 5/30; A62M 2205/3331; A62M 2205/50; A62M 2205/8206
See application file for complete search history.

(56) References Cited

U.S. PATENT DOCUMENTS 7,473,241 B2 * 1/2009 Hjertman ................ A61M 5/30
604/68
2002/0156418 A1 * 10/2002 Gonnelli ................ A61M 5/30
604/69
(Continued)

FOREIGN PATENT DOCUMENTS

JP  2005-523679 A  8/2005
JP  2007-525192 A  9/2007
(Continued)

OTHER PUBLICATIONS

Extended European Search Report dated Mar. 15, 2021 in European Application No. 18823047.8, in 8 pages.
(Continued)

*Primary Examiner* — Nathan R Price
*Assistant Examiner* — Tania Ismail
(74) *Attorney, Agent, or Firm* — Knobbe Martens Olson & Bear LLP

(57) ABSTRACT

A needleless injector pressurizes a substance to be injected having an ejection pressure defined as a pressure of the substance to be injected ejected through an ejection port. The ejection pressure is raised to a first peak pressure after pressurizing is started, is lowered to a pressure lower than the first peak pressure afterward, and then is raised to a
(Continued)

second peak pressure again. An on-completion reached depth that is an on-completion reached depth of the substance when the pressurizing portion completes pressurizing is adjustable, the on-completion reached depth being increased along with increase of the first peak pressure and being increased along with reduction of a length between peaks from a first timing at which the ejection pressure reaches the first peak pressure to a second timing at which the ejection pressure reaches the second peak pressure.

13 Claims, 11 Drawing Sheets

(52) U.S. Cl.
CPC . *A61M 2205/3331* (2013.01); *A61M 2205/50* (2013.01); *A61M 2205/8206* (2013.01)

(56) References Cited

U.S. PATENT DOCUMENTS

| | | | |
|---|---|---|---|
| 2013/0237951 A1 | 9/2013 | Oda | |
| 2013/0304017 A1 | 11/2013 | Williamson | |
| 2014/0200512 A1 | 7/2014 | Oda | |
| 2015/0057607 A9* | 2/2015 | Oda | A61M 5/30 604/69 |
| 2018/0036485 A1 | 2/2018 | Oda | |
| 2018/0056003 A1 | 3/2018 | Oda | |
| 2019/0151552 A1 | 5/2019 | Oda | |

FOREIGN PATENT DOCUMENTS

| | | |
|---|---|---|
| JP | 2008-508881 A | 3/2008 |
| JP | 2008-206477 A | 9/2008 |
| JP | 2010-503616 A | 2/2010 |
| JP | 2012-061269 A | 3/2012 |
| JP | 2012-065922 A | 4/2012 |
| WO | WO 2003/004620 A2 | 1/2003 |
| WO | WO 2005/019453 A2 | 3/2005 |
| WO | WO 2006/015373 A2 | 2/2006 |
| WO | WO 2008/047243 A2 | 4/2008 |

OTHER PUBLICATIONS

International Search Report and Written Opinion dated Sep. 18, 2018 in International Application No. PCT/JP2018/024466, in 16 pages.

* cited by examiner

NEEDLELESS INJECTOR, METHOD OF ADJUSTING ON-COMPLETION REACHED DEPTH WITH NEEDLELESS INJECTOR, AND EJECTION PARAMETER CALCULATION PROGRAM FOR NEEDLELESS INJECTOR

CROSS REFERENCE TO RELATED APPLICATIONS

This application is a U.S. National Phase of International Application No. PCT/JP2018/024466, filed on Jun. 27, 2018, which claimed priority to and the benefit of Japanese Patent Application No. 2017-125672 filed on Jun. 27, 2017, each of which is hereby incorporated by reference in their entireties.

FIELD

The present invention relates to a needleless injector that injects a substance to be injected to a target region without using an injection needle.

BACKGROUND

An injector can be exemplified as a device that administers a liquid chemical to a target region such as an organism. In recent years, a needleless injector that does not include an injection needle has been developed in view of handling facilitation, sanitation, and the like. In general, there has been implemented a needleless injector having a configuration in which a liquid chemical pressurized by a drive source such as compressed gas and a spring is ejected to a target region and the liquid chemical is administered to an inside of the target region through use of the kinetic energy of the liquid chemical. As another drive source, use of chemical combustion has been examined. As described above, the needleless injector does not have a mechanical configuration that is held in direct contact with the inside of the target region (for example, an injection needle), and hence convenience for a user is high. Meanwhile, due to absence of such mechanical configuration, it is not always easy to administer the liquid chemical to a desired part in the target region.

Here, Patent Document 1 discloses a technique of sending a liquid chemical into a desired depth of a skin structure body of an organism with a needleless injector. Specifically, the technique relates to pressurizing for ejection of an injection solution, with pressurizing control having a first pressurizing mode and a second pressurizing mode being performed. In the first pressurizing mode, after a pressure is raised to a first peak pressure, the pressure to the injection solution is lowered to a standby pressure, and thus a through passage is formed in an injection target region. In the second pressurizing mode, pressurizing is performed to the injection solution having the standby pressure, the pressure of the injection solution is raised to a second peak pressure, and thus a predetermined injection amount is injected. By performing such pressurizing control, the behavior of the injection solution in the target region is controlled.

CITATION LIST

Patent Document

[Patent Document 1] JP 2012-61269 A

SUMMARY

Technical Problem

In a related-art technique, the pressure applied to the injection solution by explosive combustion is controlled separately in the two pressurizing modes, and the injection solution is suitably ejected to an outside of the injector in the second pressurizing mode. In this manner, injection to the target region is achieved. However, highly accurate adjustment for a depth that the injection solution to be injected may reach in the target region is not mentioned at all, and hence there is room left for improvement.

In view of the problem described above, the present invention has an object to provide, to a needleless injector that injects a substance to be injected to a target region without using an injection needle, a technique of accurately adjusting a reached depth of the ejected substance to be injected in the target region.

Solution to Problem

In order to solve the above-mentioned problem, in a case where an ejection pressure of a needleless injector pressurizes a substance to be injected having two peak pressures, the present invention focuses on magnitudes of the two peak pressures and timings at which the peak pressures emerge. That is, the inventors of the present application have newly found out that these ejection parameters relating to the needleless injector dominantly influence a reached depth of the ejected substance to be injected in a target region. Therefore, the reached depth in the target region can be adjusted accurately by using these ejection parameters suitably.

Specifically, in an embodiment of the present invention, a needleless injector that injects a substance to be injected to a target region without using an injection needle includes an encapsulating portion configured to encapsulate the substance to be injected, a pressurizing portion configured to pressurize the substance to be injected encapsulated in the encapsulating portion, and a flow path including an ejection port through which the substance to be injected pressurized by the pressurizing portion is ejected to the target region. Further, in the needleless injector, the pressurizing portion pressurizes the substance to be injected having an ejection pressure defined as a pressure of the substance to be injected ejected through the ejection port. The ejection pressure is raised to a first peak pressure after pressurizing is started, is lowered to a pressure lower than the first peak pressure afterward, and then is raised to a second peak pressure again. Further, the needleless injector is capable of adjusting an on-completion reached depth that is an on-completion reached depth of the substance to be injected in the target region when the pressurizing portion completes pressurizing, the on-completion reached depth being increased along with increase of the first peak pressure and being increased along with reduction of a length between peaks from a first timing at which the ejection pressure reaches the first peak pressure to a second timing at which the ejection pressure reaches the second peak pressure.

In the needleless injector according to an embodiment of the present invention, the pressurizing portion pressurizes the substance to be injected encapsulated in the encapsulating portion, and thus the substance to be injected is ejected to the target region. An energy used for pressurizing may be a chemically-generated energy, for example a combustion energy generated by an oxidation reaction of a low explosive, a high explosive, or the like. Further, as another method, the energy for pressurizing may be generated electrically. As one example, an energy caused by a piezoelectric element or an electromagnetic actuator that is driven by applied electronic power may be employed. Further, as another method, the energy for pressurizing may be generated physically. As one example, an elastic energy of an elastic body or an internal energy of a compressed body such as compressed gas may be employed. That is, the energy for pressurizing may be any energy as long as the energy enables ejection of the substance to be injected with the needleless injector. Therefore, the energy for pressurizing may be a complex type energy obtained by combining a combustion energy, an electronic energy, and an internal energy such as an elastic energy as appropriate.

Further, as the substance to be injected ejected from the needleless injector according to an embodiment of the present invention, a component expected to have effects in the target region or a component expected to exert a predetermined function in the target region can be exemplified. Thus, as long as ejection with the energy for pressurizing described above can be achieved, a physical mode of the substance to be injected may be present in a state of being dissolved in liquid, or may be in a state of simply being mixed without being dissolved in liquid. As one example, the predetermined substance to be sent includes vaccine for intensifying an antibody, a protein for cosmetic enhancement, a cultured cell for hair regeneration, and the like, and is included in a liquid medium in an ejectable manner. The substance to be injected is formed in this way. Note that, the medium is preferably a medium that does not hinder the above-mentioned effect and function of the predetermined substance in a state of being injected inside the target region. As another method, the medium may be a medium that exerts the above-mentioned effect and function by acting together with the predetermined substance in the state of being injected inside the target region.

The ejection pressure of the substance to be injected, which is formed by pressurizing by the pressurizing portion, is raised to a first peak pressure after pressurizing is started, is lowered to a pressure lower than the first peak pressure afterward, and is raised to a second peak pressure again. The first peak pressure is a characteristic pressure mainly required when the ejected substance to be injected penetrates the surface of the target region and enters the inside at the initial stage. The second peak pressure that emerges later is a characteristic pressure required when most of the substance to be injected is sent into the target region. Note that, the ejection pressure is defined as a pressure of the substance to be injected that is ejected through the ejection port, and is a pressure applied to the substance to be injected immediately after ejection through the ejection port, that is, in the vicinity of the ejection port, and a pressure for the substance to be injected to be ejected through the ejection port. In a physical sense, as the distance from the ejection port grows due to ejection, the pressure applied to the substance to be injected is smaller. The ejection pressure in an embodiment of the present invention is a pressure applied to the substance to be injected at the time when the substance to be injected is ejected from the needleless injector to the target region.

The inventors of the invention of the present application have now discovered that, in the needleless injector that achieves the ejection pressure transitioning with the two peak pressures as described above, the magnitude of the first peak pressure in the ejection pressure transition and the length between the peaks dominantly determine the on-completion reached depth of the substance to be injected in the target region. Herein, the on-completion reached depth indicates a depth reached by the substance to be injected in the target region in the ejection direction (advance direction) when the pressurizing portion completes pressurizing, for example, when the ejection pressure is lowered to around zero after the second peak pressure. In other words, the on-completion reached depth indicates a depth by which the substance to be injected directly advances in the target region due to pressurizing by the pressurizing portion, and is different from a depth in a case where the substance to be injected is diffused after ejection in the target region over time (hereinafter, referred to as "diffusion reached depth"). However, the diffusion reached depth is formed after the on-completion reached depth, and hence the on-completion reached depth can be considered as an element that greatly influences the diffusion reached depth.

Further, specifically, there has been found a trend that the on-completion reached depth is increased along with increase of the first peak pressure and the on-completion reached depth is increased along with reduction of the length between the peaks. The on-completion reached depth is considered to be increased because the energy of the substance to be injected that first advances in the target region is increased along with increase of the first peak pressure at the ejection initial stage. Moreover, it is considered that the substance to be injected along with the second peak pressure can reach a deeper part because, when the length between the peaks is reduced, a time period required for the target region, in which the substance to be injected advances along with the first peak pressure, to return to the original state by the time the substance to be injected subsequently advancing along with the second peak pressure reaches the target region, is shorter. Further, the first peak pressure and the length between the peaks are parameters having an extremely strong correlation when considering the on-completion reached depth. Thus, in consideration of both the parameters together, the on-completion reached depth to be achieved can be adjusted more accurately. This finally leads to accurate adjustment of the diffusion reached depth.

Moreover, it has been found out that, as an element that dominantly determines the on-completion reached depth of the substance to be injected, a lowering state of the pressure emerging between the first peak pressure and the second peak pressure can be substantially eliminated, which is worth mentioning in particular. With this, even when the ejection pressure transition from the first peak pressure to the second peak pressure and all pressure transition after the second peak pressure are not designed, the on-completion reached depth of the substance to be injected can be adjusted at a sufficiently satisfactory accuracy by achieving the ejection pressure transition including the desired first peak pressure and the desired length between the peaks. Thus, a load required for the adjustment (for example, a load for adjusting pressurizing with the pressurizing portion) can be drastically alleviated.

Herein, in the needleless injector described above, the on-completion reached depth of the substance to be injected in the target region may be further adjustable, the on-completion reached depth being increased along with increase of the second peak pressure. As described above, the second peak pressure is included in the adjustment parameters of the on-completion reached depth, and thus the on-completion reached depth can be adjusted more accurately. Further, the second peak pressure itself is a parameter relating to the above-mentioned length between the peaks, and hence does not aimlessly complicate the adjustment of the on-completion reached depth.

Further, in the needleless injector described above, the on-completion reached depth may be further adjustable by adjusting an additional reached depth from a reached depth of the substance to be injected at the first timing in the target region to the on-completion reached depth, the additional reached depth being increased along with increase of the second peak pressure and being increased along with reduction of the first peak pressure. Herein, the focus is made on the additional reached depth being an additional reached depth formed from the reached depth of the substance to be injected from the first timing to the second timing. When the process in which the substance to be injected advances in the target region and reaches the on-completion reached depth is divided into a process up to the first timing and a process thereafter, the additional reached depth indicates a reached depth formed in the latter half process. A step of forming the additional reached depth can be considered as a step of finely adjusting the on-completion reached depth, so to speak. Therefore, as a result of keen study of the inventors of the present application, it has been found out that the additional reached depth is adjustable with the first peak pressure and the second peak pressure. With this, the on-completion reached depth can be adjusted more finely, and hence adjustment accuracy of the on-completion reached depth can be improved.

Herein, the needleless injector described above may further include an igniter including an ignition charge and a gas generating agent that is disposed in a combustion chamber into which a combustion product generated by combustion of the ignition charge flows and that is combusted by the combustion product and generates predetermined gas. Further, the ignition charge is any one of an explosive containing zirconium and potassium perchlorate, an explosive containing titanium hydride and potassium perchlorate, an explosive containing titanium and potassium perchlorate, an explosive containing aluminum and potassium perchlorate, an explosive containing aluminum and bismuth oxide, an explosive containing aluminum and molybdenum oxide, an explosive containing aluminum and copper oxide, an explosive containing aluminum and iron oxide, or an explosive composed of a combination of a plurality of the explosives. Further, the gas generating agent is formed to be combusted at a combustion speed lower than a combustion speed of the ignition charge. For example, as the gas generating agent, a single base smokeless explosive and various types of gas generating agents used in a gas generator for an air bag and a gas generator for a seat belt pretensioner may be used. Further, the pressurizing portion causes the ejection pressure of the substance to be injected to reach the first peak pressure with a combustion pressure of the ignition charge by operating the igniter, and causes the ejection pressure of the substance to be injected to reach the second peak pressure with a combustion pressure of the gas generating agent that is combusted subsequent to the ignition charge. In this manner, the ignition charge and the gas generating agent are combusted in a linked manner, and thus the substance to be injected can be pressurized by the pressurizing portion as described above.

As characteristics of the above-mentioned ignition charge, the combustion product is gas at a high temperature but does not include a gas component at a room temperature, and hence the combustion product is condensed immediately after the ignition. As a result, the ejection pressure is rapidly lowered after reaching the first peak pressure. After that, the gas generating agent is combusted, and the ejection pressure reaches the second peak pressure relatively gradually. It has been found out that adjustment of the on-completion reached depth described above can be performed suitably by performing the pressure transition formation of the ejection pressure at the initial stage mainly with the ignition charge and performing the transition formation of the ejection pressure afterward with the gas generating agent as described above. Further, the ejection parameters for the needleless injector such as the first peak pressure and the length between the peaks of the ejection pressure formed through pressurizing can be adjusted with parameters relating to combustion of the ignition charge and the gas generating agent, for example, through adjustment of an amount, a shape, an disposal relationship in the needleless injector, or the like of the ignition charge or the gas generating agent.

Further, the invention of the present application can be understood from an aspect of an adjustment method of adjusting an on-completion reach depth of a substance to be injected in a target region when pressurizing is completed, which is performed with the needleless injector configured to inject the substance to be injected to the target region without using an injection needle by pressurizing the substance to be injected that is encapsulated and ejecting the substance to be injected that is pressurized through an ejection port to the target region. In this case, the needleless injector pressurizes the substance to be injected having an ejection pressure defined as a pressure of the substance to be injected ejected through the ejection port. The ejection pressure is raised to a first peak pressure after pressurizing is started, is lowered to a pressure lower than the first peak pressure afterward, and then is raised to a second peak pressure again. Further, the adjustment method includes setting the first peak pressure in accordance with a first adjustment reference that the on-completion reached depth is increased along with increase of the first peak pressure, setting a length between peaks in accordance with a second adjustment reference that the on-completion reached depth is increased along with reduction of the length between the peaks required from a first timing at which the ejection pressure reaches the first peak pressure to a second timing at which the ejection pressure reaches the second peak pressure, and determining predetermined pressurizing specifications relating to pressurizing of the substance to be injected, based on the first peak pressure and the length between the peaks that are set. By following the adjustment method described above, the on-completion reached depth to be achieved can be adjusted more accurately, and a load required for the adjustment can be drastically alleviated. Note that, the predetermined pressurizing specifications are specifications relating to supply of an energy to be applied for pressurizing the substance to be injected, and thus the set first peak pressure and the set length between the peaks emerge in the ejection pressure transition of the substance to be injected. For example, in a case where the energy is supplied by combustion of the ignition charge and the gas generating agent as described above, an ignition charge and a gas generating agent with an amount, a shape, or the like, which enable combustion thereof, can be exemplified. Further, the technical ideas disclosed in relation to the needleless injector described above are applicable to the invention relating to the adjustment method described above as long as technical inconsistency is not caused.

Further, as another method, the invention of the present application can be understood from an aspect of a program causing a processing device to calculate predetermined ejection parameters for the needleless injector for adjusting an on-completion reach depth of a substance to be injected in a target region when pressurizing is completed, which is performed with the needleless injector configured to inject the substance to be injected to the target region without using an injection needle by pressurizing the substance to be injected that is encapsulated and ejecting the substance to be injected that is pressurized through an ejection port to the target region. In this case, the needleless injector pressurizes the substance to be injected having an ejection pressure defined as a pressure of the substance to be injected ejected through the ejection port. The ejection pressure is raised to a first peak pressure after pressurizing is started, is lowered to a pressure lower than the first peak pressure afterward, and then is raised to a second peak pressure again. Further, the program causes the processing device to execute calculating the first peak pressure in accordance with a first adjustment reference that the on-completion reached depth is increased along with increase of the first peak pressure, calculating a length between peaks in accordance with a second adjustment reference that the on-completion reached depth is increased along with reduction of the length between the peaks required from a first timing at which the ejection pressure reaches the first peak pressure to a second timing at which the ejection pressure reaches the second peak pressure, and determining predetermined pressurizing specifications relating to pressurizing of the substance to be injected, based on the first peak pressure and the length between the peaks that are set. The predetermined pressurizing specifications are as described above. Through use of the ejection parameter calculation program for the needleless injector, calculation of the ejection parameters, which achieves a more accurate on-completion reached depth, can be facilitated. Further, the invention of the present application can be understood from an aspect of a processing device in which the above-mentioned program is installed or a recording medium that records the program. Note that, the technical ideas disclosed in relation to the needleless injector described above are applicable to the invention relating to the ejection parameter calculation program for the needleless injector, the processing device in which the program is installed, or the recording medium that records the program as long as technical inconsistency is not caused.

Advantageous Effects of Invention

With the needleless injector that injects the substance to be injected to the target region without using an injection needle, the reached depth of the ejected substance to be injected in the target region can be adjusted accurately.

DESCRIPTION OF EMBODIMENTS

With reference to the drawings, a needleless injector 1 according to an embodiment of the invention of the present application (herein, simply referred to as "injector") is described below. The injector 1 is a needleless injector that ejects an injection solution, which corresponds to a substance to be injected in the present application, to a target region through use of a combustion energy of an explosive, that is, a device that injects the injection solution to the target region without using an injection needle. The injector 1 is described below.

Note that, configurations of the following embodiment are provided as examples, and the invention of the present application is not limited to the configurations of the embodiment. Note that, in the present embodiment, as terms indicating a relative positional relationship in a longitudinal direction of the injector 1, "distal end side" and "base end side" are used. "Distal end side" indicates a side close to the distal end of the injector 1 described later, that is, a position close to an ejection port 31a, and "base end side" indicates a direction opposite to "distal end side" in the longitudinal direction of the injector 1, that is, a direction to a side of an drive portion 7.

Configuration of Injector 1

Figure 1:
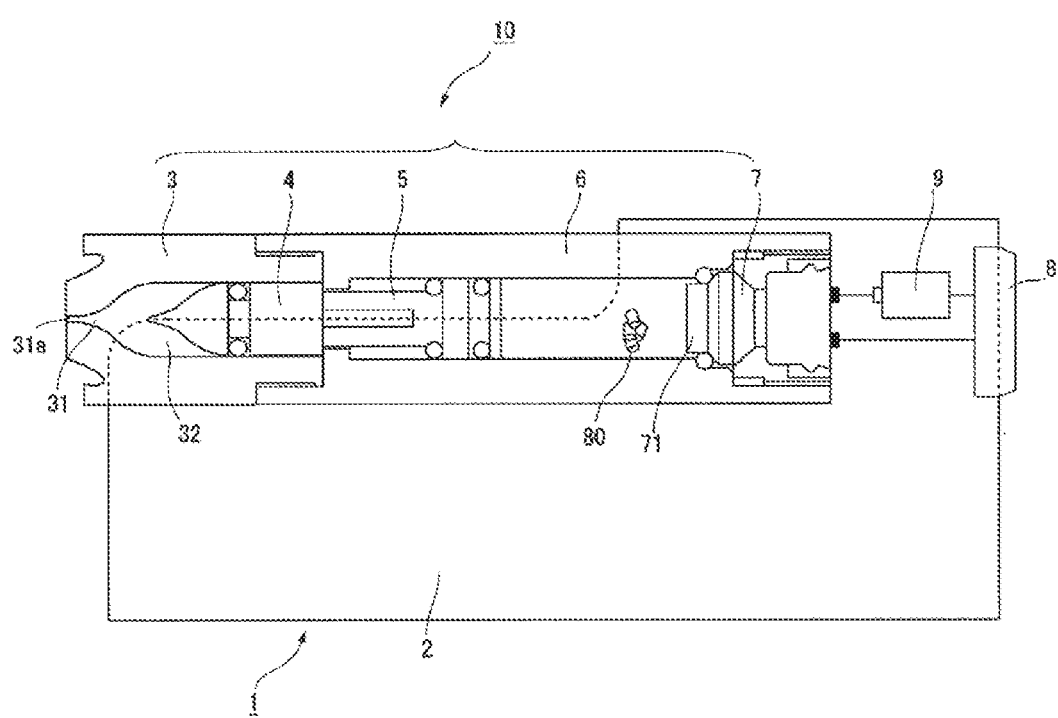
FIG. 1 is a view illustrating a schematic configuration of an injector driven by an explosive.

Herein, FIG. 1 is a view illustrating a schematic configuration of the injector 1, and is a cross-sectional view of the injector 1 taken along the longitudinal direction. The injector 1 is obtained by attaching a device assembly 10 to a housing 2. The device assembly 10 is obtained by integrally assembling a sub-assembly 10A (see FIG. 2A described later) formed of a syringe portion 3 and a plunger 4 described later and a sub-assembly 10B (see FIG. 2B described later) formed of an injector body 6, a piston 5, and the drive portion 7. Note that, in the following description in the present application, the injection solution administered to the target region by the injector 1 is formed of a liquid medium including a predetermined substance, which exerts an effect or a function expected in the target region. In the injection solution, the predetermined substance may be in a state of being dissolved in liquid being a medium, or may be in a state of being simply mixed instead of being dissolved.

For example, examples of the predetermined substance included in the injection solution include an organism-derived substance and a substance with a desired bioactivity, which can be ejected to the target region being an organism. For example, examples of the organism-derived substance include DNA, RNA, a nucleic acid, an antibody, and a cell. Examples of the substance with a desired bioactivity include various substances exerting pharmacological or therapeutic effects, which are exemplified by, low molecule medicine, an inorganic substance such as metal particles for thermotherapy or radiotherapy, and a carrying body functioning as a carrier. Further, the liquid being the medium of the injection solution is only required to be a substance suitable for administering the predetermined substance exemplified by those substances to the target region, and may be aqueous or oleaginous, which is not limited. Further, viscosity of the liquid being the medium is not particularly limited as long as the predetermined substance can be ejected by the injector 1. Further, the target region being an ejection target of the injection solution is a region to which the above-mentioned predetermined substance is to be administered, and may be exemplified by, for example, a cell or a tissue of an organism (skin or the like), and an organ (an eyeball, a heart, a liver, or the like). Note that, within a range of not causing a problem, an organism component in a state of being cut from an organism body can be set as the target region. That is, ex-vivo ejection of the predetermined substance to the target region (a tissue or an organ) and in-vitro ejection of the predetermined substance to the target region (a cultured cell or a cultured tissue) are included within an operation range of the injector according to the present embodiment.

The device assembly 10 is freely attachable to and detachable from the housing 2. A filling chamber 32 (see FIG. 2A) formed between the syringe portion 3 and the plunger 4 included in the device assembly 10 is filled with an injection solution, and the device assembly 10 is a unit that is replaced each time the injection solution is ejected. Meanwhile, the housing 2 includes a battery 9 that supplies power to an igniter 71 included in the drive portion 7 of the device assembly 10. A user performs an operation of pressing down a button 8 provided to the housing 2, and thus the power supply from the battery 9 is performed between an electrode on the housing 2 side and an electrode on the drive portion 7 side of the device assembly 10 via a wired line. Note that, the electrode on the housing 2 side and the electrode on the drive portion 7 side of the device assembly 10 are designed in shapes and at positions, and thus both the electrodes are automatically held in contact with each other when the device assembly 10 is attached to the housing 2. Further, the housing 2 is a unit that can be repeatedly used as long as power that can be applied to the drive portion 7 is left in the battery 9. Further, in the housing 2, in a case where power of the battery 9 is exhausted, the housing 2 may be used continuously by replacing only the battery 9.

Figure 2A:
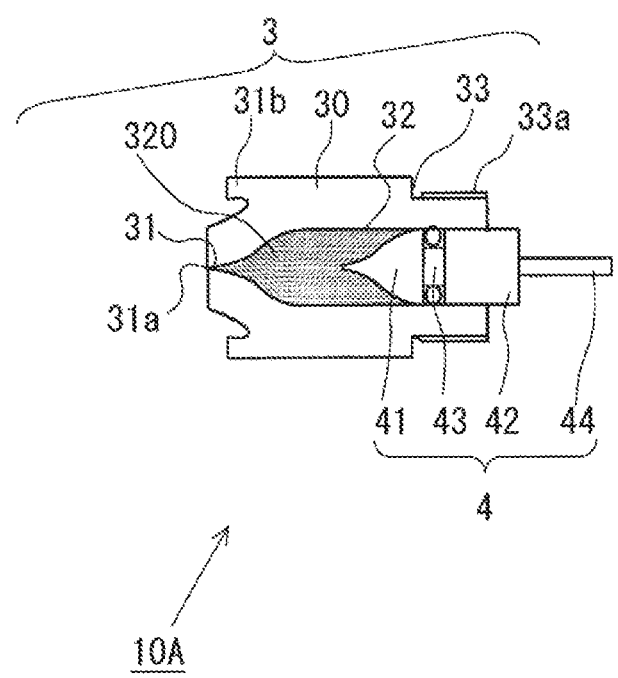
FIG. 2A is a view illustrating a schematic configuration of a first sub-assembly that forms a device assembly incorporated in the injector illustrated in FIG. 1.
Figure 2B:
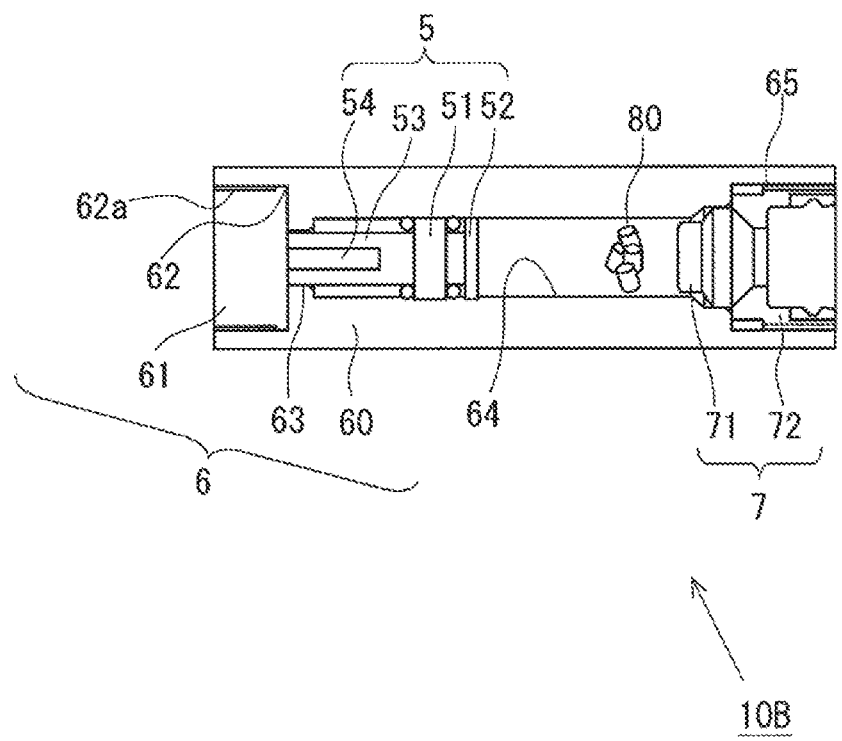
FIG. 2B is a view illustrating a schematic configuration of a second sub-assembly that forms the device assembly incorporated in the injector illustrated in FIG. 1.

Now, with reference to FIG. 2A and FIG. 2B, configurations of the sub-assemblies 10A and 10B and detailed configurations of the syringe portion 3, the plunger 4, the piston 5, the injector body 6, the drive portion 7 included in the sub-assemblies are described. The syringe portion 3 includes a nozzle portion 31 including the filling chamber 32 being a space capable of storing the injection solution. The plunger 4 is disposed in the sub-assembly 10A in a manner slidable in the filling chamber 32.

For a body 30 of the syringe portion 3, nylon 6-12, polyarylate, polybutylene terephthalate, polyphenylene sulphide, a liquid crystal polymer, or the like, which are publicly known, may be used. Further, a filler such as glass fibers and glass filler may be contained in those resins. 20 to 80 mass % of glass fibers may be contained in polybutylene terephthalate, 20 to 80 mass % of glass fibers may be contained in polyphenylene sulphide, or 20 to 80 mass % of minerals may be contained in a liquid crystal polymer.

Further, in the filling chamber 32 formed inside the body 30, the plunger 4 is disposed in a manner slidable in the nozzle portion 31 direction (the distal end side direction). A space formed between the plunger 4 and the body of the syringe portion 3 is a space in which an injection solution 320 is encapsulated. Herein, the plunger 4 slides in the filling chamber 32. Then the injection solution 320 stored in the filling chamber 32 is pressed, and is ejected through the ejection port 31a provided on the distal end side of the nozzle portion 31. Thus, the plunger 4 is formed of a material that advances smoothly in the filling chamber 32 and prevents the injection solution 320 from leaking from the plunger 4 side. Specific examples of the material of the plunger 4 include butyl rubber and silicon rubber. Further, there may be exemplified a styrene-based elastomer or a hydrogenated styrene-based elastomer, or a substance obtained by mixing a styrene-based elastomer or a hydrogenated styrene-based elastomer with polyolefin such as polyethylene, polypropylene, polybutene, and an α-olefin copolymer, oil such as liquid paraffin and process oil, or a powder inorganic substance such as talc, cast, and mica. Further, as the material of the plunger 4, there may be employed a polyvinyl chloride-based elastomer, an olefin-based elastomer, a polyester-based elastomer, a polyamide-based elastomer, a polyurethane-based elastomer, various rubber materials (particularly, a vulcanized material) such as natural rubber, isoprene rubber, chloroprene rubber, nitrile butadiene rubber, and styrene butadiene rubber, or a mixture thereof. Further, for the purpose of securing and adjusting advance between the plunger 4 and the syringe portion 3, the surface of plunger 4 and the surface of the filling chamber 32 of the syringe portion 3 may be subjected to coating or surface finishing with various substances. Examples of the coating agent may include polytetrafluoroethylene (PTFE), silicon oil, diamond-like carbon, nano diamond, and the like.

Herein, as illustrated in FIG. 2A, the plunger 4 includes a head portion 41 and a barrel portion 42, which may be coupled by a neck portion 43 having a diameter smaller than a diameter of the head portion 41 and the barrel portion 42. The neck portion 43 has a small diameter as described above, and thus, an accommodation space for an O-ring being a seal member is formed. Note that, an outline of the head portion 41 on the distal end side has a shape that substantially matches with an outline of an inner wall surface of the nozzle portion 31. With this, when the plunger 4 slides to the nozzle portion 31 side at the time of ejection of the injection solution and reaches the deepest position located deepest in the filling chamber 32, the space formed between the plunger 4 and the inner wall surface of the nozzle portion 31 can be reduced as much as possible, and the injection solution 320 can be prevented from remaining in the filling chamber 32 and being wasted. However, the shape of the plunger 4 is not limited to a particular shape as long as desired effects can be obtained with the injector according to the present embodiment.

Moreover, a rod portion 44, which extends from an end surface of the barrel portion 42 on the base end side in a direction to the base end side, is provided to the plunger 4. The rod portion 44 has a diameter sufficiently smaller than the barrel portion 42, which enables a user to grip the rod portion 44 in a manner movable in the filling chamber 32. Further, a length of the rod portion 44 is determined. Thus, even when the plunger 4 is at the deepest position in the filling chamber 32 of the syringe portion 3, the rod portion 44 protrudes from an end surface of the syringe portion 3 on the base end side, and a user can grip the rod portion 44.

Herein, description is returned to the syringe portion 3. A flow path, which is provided to the nozzle portion 31 on the syringe portion 3 side, has an inner diameter formed smaller than an inner diameter of the filling chamber 32. With the configuration described above, the injection solution 320 pressurized to a high pressure is ejected to the outside through the ejection port 31a of the flow path. In view of this, an annular shield portion 31b that surrounds a periphery of the ejection port 31a is provided on the distal end side of the syringe portion 3, that is, in the vicinity of the nozzle portion 31. For example, when the ejection port 31a is pressed against the target region such as a surface of human skin and the injection solution is ejected, the shield portion 31b can perform shielding and prevent the ejected injection solution from scattering in the periphery. Note that, the skin is pushed down to a certain degree when the ejection port is pressed against the skin, which can improve contact between the ejection port and the skin and prevent the injection solution from scattering. In view of this, as illustrated in FIG. 2A, the distal end of the nozzle portion 31 at which the ejection port 31a is positioned may slightly protrude from an end surface of the shield portion 31b in the ejection direction of the injection solution.

Further, a screw portion 33a that couples the injector body 6 on the sub-assembly 10B described later and the syringe portion 3 with each other is formed on a neck portion 33 positioned on the base end side of the syringe portion 3. A diameter of the neck portion 33 is set to be smaller than a diameter of the body 30.

Next, with reference to FIG. 2B, the sub-assembly 10B including the piston 5, the injector body 6, and the drive portion 7 is described. The piston 5 is pressurize by a combustion product generated at the igniter 71 of the drive portion 7, and slides in a through-hole 64 formed inside a body 60 of the injector body 6. Herein, a coupling recessed portion 61 is formed in the injector body 6 on the distal end side with the through-hole 64 as a reference. The coupling recessed portion 61 is a part that is coupled with the neck portion 33 of the syringe portion 3 described above, and a crew portion 62a that is threaded to the screw portion 33a provided to the neck portion 33 is formed on a side wall surface 62 of the coupling recessed portion 61. Further, the through-hole 64 and the coupling recessed portion 61 are communicated with each other with a communication portion 63, and a diameter of the communication portion 63 is set to be smaller than a diameter of the through-hole 64. Further, a recessed portion 65 for the drive portion is formed in the injector body 6 on the base end side with the through-hole 64 as a reference. The drive portion 7 is to be disposed in the recessed portion 65 for the drive portion.

Further, the piston 5 is formed of metal, and includes a first barrel portion 51 and a second barrel portion 52. The piston 5 is disposed in the through-hole 64. Thus, the first barrel portion 51 is oriented to the coupling recessed portion 61 side, and the second barrel portion 52 is oriented to the recessed portion 65 for the drive portion. While the first barrel portion 51 and the second barrel portion 52 face an inner wall surface of the through-hole 64 of the injector body 6, the piston 5 slides in the through-hole 64. Note that, a coupling portion smaller than a diameter of each of the barrels couples the first barrel portion 51 and the second barrel portion 52 with each other, and an O-ring or the like that improves adhesiveness with the inner wall surface of the through-hole 64 is disposed in a resultant space formed between both the barrels. Further, the piston 5 may be formed of a resin, and in such case, metal may be used together for a part to which heat resistance and pressure resistance are required.

Herein, a pressing pillar portion 53 is provided to an end surface of the first barrel portion 51 on the distal end side. The pressing pillar portion 53 has a diameter smaller than a diameter of the first barrel portion 51 and smaller than a diameter of the communication portion 63 of the injector body 6. An accommodation hole 54 is opened and provided in an end surface of the pressing pillar portion 53 on the distal end side. The accommodation hole 54 has a diameter equal to or larger than a diameter of the rod portion 44, and has a depth larger than a length of the rod portion 44. Thus, when the piston 5 is pressurized by the combustion product of the igniter 71 via the end surface of the pressing pillar portion 53 on the distal end side, the combustion energy can be imparted to the end surface of the barrel portion 42 of the plunger 4 on the base end side. Note that, the shape of the piston 5 is not limited to the shape described in FIG. 2B.

Next, the drive portion 7 is described. The drive portion 7 includes a body 72 formed in a tubular shape and the igniter 71 formed therein as an electric igniter that combusts ignition charge and generates an energy for ejection. The drive portion 7 is disposed in the recessed portion 65 for the drive portion as described above, and thus the combustion energy by the igniter 71 is imparted to the second barrel portion 52 of the piston 5. Specifically, the body 72 of the drive portion 7 may be obtained by fixing an injection molded resin to a metal collar. The injection molding may be performed by a publicly known method. The same resin material as the body 30 of the syringe portion 3 may be employed as a resin material for the body 72 of the drive portion 7.

Herein, a combustion energy used in the igniter 71 for the ignition charge is an energy for the injector 1 to eject the injection solution to the target region. Note that, examples of the ignition charge include an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), an explosive containing aluminum and iron oxide (AFO), or an explosive composed of a combination of a plurality of these explosives. These explosives exhibit characteristics that, although the explosives generate high-temperature and high-pressure plasma during combustion immediately after ignition, when the combustion product condenses at room temperature, the explosives do not contain gaseous components and hence the pressure generated decreases abruptly. An explosive other than these may be used as the ignition charge as long as appropriate ejection of the injection solution can be performed.

Further, in addition to the above-mentioned ignition charge, a gas generating agent 80 that is combusted by the combustion product generated by explosive combustion at the igniter 71 and generates gas is disposed in the injector 1, and thus transition of the pressure to be applied to the injection solution via the piston 5 is adjusted. This disposal place is, for example, as illustrated in FIG. 1 and FIG. 2B, a place that may be exposed to the combustion product from the igniter 71. Further, as another method, the gas generating agent 80 may be disposed in the igniter 71 as disclosed in WO 01-031282, JP 2003-25950 A, and the like. As one example of the gas generating agent, there may be exemplified a single base smokeless explosive formed of 98 mass % of nitrocellulose, 0.8 mass % of diphenylamine, and 1.2 mass % of potassium sulfate. Further, various types of gas generating agents used in a gas generator for an air bag and a gas generator for a seat belt pretensioner may be used. A combustion completion time period of the gas generating agent can be changed by adjusting a dimension, a size, a shape, and particularly, a surface shape of the gas generating agent at the time of being disposed in the through-hole 64. With this, the transition of the pressure applied to the injection solution is adjusted, and an ejection pressure can be transitioned in a desired manner.

Note that, under a state in which the plunger 4 is inserted to the deepest position, the ejection port 31a is immersed in a container filled with the injection solution, and while maintaining this state, the plunger 4 is pulled back to the opening side of the filling chamber 32, that is, to the base end side of the syringe portion 3. In this manner, filling of the injection solution 320 in the sub-assembly 10A is performed. Note that, in this state, the plunger 4 is pulled back until the end surface of the barrel portion 42 of the plunger 4 on the base end side arrives at a position slightly protruding from the end surface of the syringe portion 3 on the base end side.

Further, in the sub-assembly 10B, the piston 5 is first inserted from the base end side of the injector body 6 illustrated in FIG. 2B. In this state, the piston 5 is inserted into the through-hole 64, and thus the pressing pillar portion 53 is oriented to the coupling recessed portion 61 side. Further, an end surface of the piston 5 of the distal end side, that is, the end surface of the pressing pillar portion 53 on the distal end side in which the accommodation hole 54 is opened is positioned, and thus the end surface protrudes from a bottom of the coupling recessed portion 61 (a surface orthogonal to the side wall surface 62) by a predetermined amount. At the time of positioning the piston 5, a publicly known technique such as setting of a mark for positioning in the through-hole 64 or use of a tool for positioning may be used as appropriate. Further, the gas generating agent 80 is disposed in the through-hole 64, and the drive portion 7 is attached to the recessed portion 65 for the drive portion. Note that, a fixing force of the through-hole 64 of the piston 5 is set to an extent that the piston 5 can slide in the through-hole 64 in a sufficiently smooth manner by a pressure received from the combustion product of the igniter 71 of the drive portion 7, and to an extent that the position of the piston 5 does not fluctuate while resisting against a force that the piston 5 receives from the plunger 4 at the time of attaching the sub-assembly 10A to the sub-assembly 10B.

The sub-assembly 10A having such configuration is attached to the sub-assembly 10B with screwing together the screw portions 33a and 62a. In this manner, the device assembly 10 is formed. In this state, as the coupling of both the assemblies progresses, the rod portion 44 of the plunger 4 advances, and is accommodated in the accommodation hole 54 provided in the pressing pillar portion 53 of the piston 5. Finally, the end surface of the pressing pillar portion 53 on the distal end side is held in contact with the end surface of the barrel portion 42 of the plunger 4 on the base end side. Note that, the accommodation hole 54 has a size that is large enough to accommodate the rod portion 44, and hence, in this contact state, a deep inner wall surface of the accommodation hole 54 (particularly, a bottom surface of the accommodation hole 54) is not held in contact with an end of the rod portion 44 on the base end side. Thus, the rod portion 44 does not receive a load from the piston 5 side. Moreover, the position of the piston 5 is fixed in the through-hole 64 with a sufficient frictional force as described above. Thus, when the screwing together progresses to the final position, the plunger 4 is pressed by the pressing pillar portion 53, and advances to the ejection port 31a side, and the plunger 4 is positioned in the syringe portion 3. Note that, a part of the injection solution 320 in accordance with an amount of the plunger 4 that is pushed out is discharged through the ejection port 31a.

When the plunger 4 is positioned at the final position as described above, formation of the device assembly 10 is completed. In the device assembly 10, the piston 5 is positioned at a predetermined position with respect to the injector body 6. With the piston 5 as a reference, the final position of the plunger 4 in the filling chamber 32 of the syringe portion 3 is automatically determined. The final position of the plunger 4 is a position uniquely determined in the device assembly 10, and hence an amount of the injection solution 320 that is finally stored in the filling chamber 32 can be a predetermined amount determined in advance.

Further, the device assembly 10 is attached to the housing 2, and a user presses down the button 8 under a state in which the ejection port 31a is held in contact with the target region. With this, the injection solution 320 is pressurized via the piston 5 and the plunger 4, and ejection is performed. Then, the injection solution 320 is injected in the target region.

Figure 3:
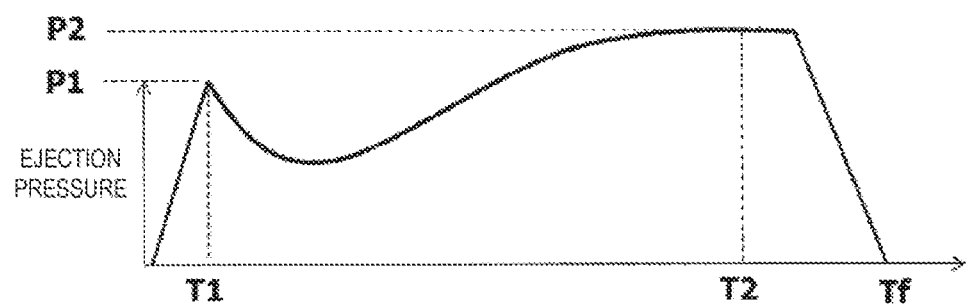
FIG. 3 is a view illustrating ejection pressure transition of an injection solution ejected by the injector illustrated in FIG. 1.
Figure 4:
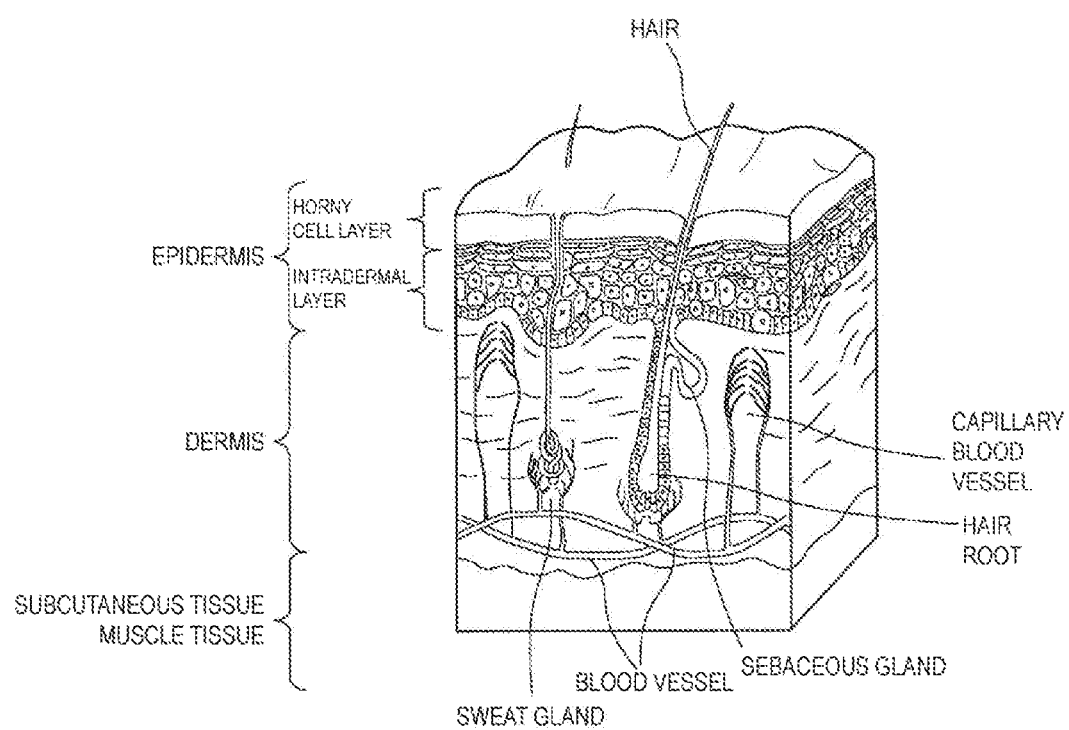
FIG. 4 is a view illustrating a structural body of skin being an injection target region.

Herein, FIG. 3 shows transition of a pressure of the injection solution ejected through the ejection port 31a at the time of performing ejection of the injection solution by driving the drive portion 7 in the injector 1 (hereinafter, simply referred to as "ejection pressure"). In FIG. 3, a horizontal axis indicates elapsed time, and a vertical axis indicates an ejection pressure. Note that, the ejection pressure can be measured through use of a related-art technique. For example, similarly to the measurement method described in JP 2005-21640 A, an ejection force may be measured by a method in which a force of ejection is applied and dispersed to a diaphragm of a load cell disposed downstream of the nozzle and output from the load cell is collected by a data collection device via a detection amplifier and is stored as an ejection force (N) for every hour. The ejection force measured in this manner is divided by an area of the ejection port 31a of the injector 1, and thus the ejection pressure is calculated. Note that, in the example shown in FIG. 3, ZPP (including zirconium and potassium perchlorate) is employed as the ignition charge in the igniter 71 in the drive portion 7, and transition of the ejection pressure obtained by disposing the gas generating agent in the through-hole 64 is given.

Here, the ejection pressure transition shown in FIG. 3 is transition of the ejection pressure from an initial point at which the operation button 8 is pressed in the drive portion 7, the transition during a time period from the combustion start to a time at which the ejection pressure is substantially zero. Note that, the initial point does not indicate rise of the ejection pressure, but is shifted by a slight time period. This is because it takes a certain time period to combust the ignition charge, cause the piston 5 to advance by the combustion energy, pressurize the injection solution, and eject the injection solution through the ejection port 31a. Herein, in the injector 1, first, the ignition charge in the igniter 71 is combusted, and then the gas generating agent 80 is combusted as described above. With this, in the ejection pressure transition, two peak pressures P1 and P2 respectively emerge in correspondence with the timings of the combustion. That is, the first peak pressure P1 that forms sudden pressure transition at the initial stage of the ejection pressure transition emerges due to the ignition charge that is combusted at a relatively high combustion speed. A timing at which the first peak pressure P1 emerges is referred to as a first timing T1. When the ignition charge is combusted, the combustion product generated herein is exposed to the gas generating agent, and hence combustion of the gas generating agent 80 is started. However, the above-mentioned ignition charge is in a gas form at a high temperature, but does not include a gaseous component at a room temperature. Thus, the ejection pressure is lowered immediately after the first timing T1. Meanwhile, the gas generating agent 80 is combusted at a lower combustion speed as compared to the ignition charge, and hence, even when combustion of the gas generating agent 80 is started, rise of the ejection pressure is relatively slow as compared to a process of reaching the first peak pressure. Thus, the second peak pressure P2 emerges at a second timing T2 delayed from the first timing T1. Note that, after the second peak pressure P2, the ejection pressure is gradually lowered, and the ejection pressure is substantially zero at a pressurizing completion timing Tf.

Figure 5A:
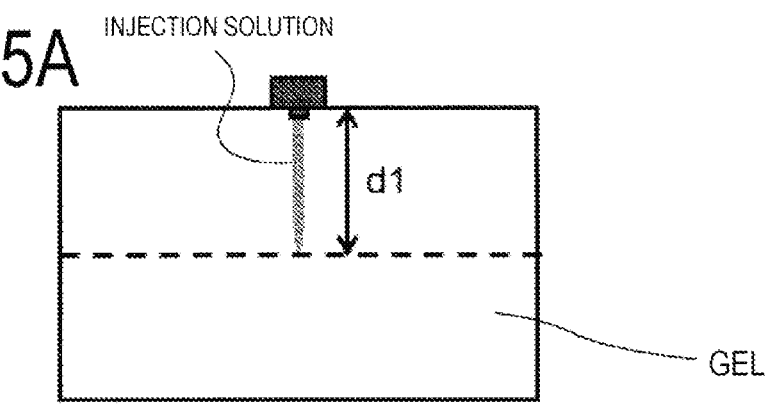
FIG. 5A is a view schematically illustrating a distribution state of the injection solution ejected by the injector illustrated in FIG. 1, which is formed in gel over time.
Figure 5B:
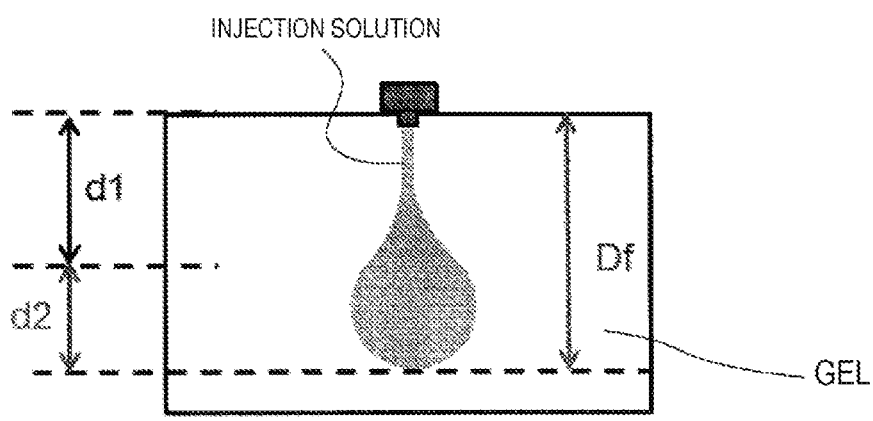
FIG. 5B is a view schematically illustrating a distribution state of the injection solution ejected by the injector illustrated in FIG. 1, which is formed in gel over time.

As described above, the injector 1 may be described as a device that forms the ejection pressure shown in FIG. 3 and pressurizes the injection solution. The injection solution to which such ejection pressure is applied physically acts on the target region, penetrates the surface of the target region, and enters the inside. Thus, injection of the injection solution to the target region is achieved. Herein, an example of the target region of the injector 1 includes a skin structure body of an organism of a human, a farm animal, or the like. FIG. 4 schematically illustrates an anatomical structure of human skin. The human skin has a layered structure including epidermis, dermis, a subcutaneous tissue, and a muscle tissue in the order from the skin surface side in a depth direction. Further, the epidermis can be sectionalized into a horny cell layer and an intradermal layer in a layered manner. Main cells constituting tissues or the like and characteristics of the tissues differ among the respective layers of the skin structure body.

Specifically, the horny cell layer is mainly formed of a keratinocyte, and is positioned on the outermost surface side of the skin. Thus, the horny cell layer has a function of a so-called barrier layer. In general, the horny cell layer has a thickness of from substantially 0.01 mm to substantially 0.015 mm, and protects the surface with the keratinocyte. Thus, relatively high strength is required for physically shielding the inside of the human body from an external environment to some extent. Further, the intradermal layer is constituted of a dendritic cell (a Langerhans cell) and a chromocyte (melanocyte). The horny cell layer and the intradermal layer form the epidermis, and the epidermis has a thickness of from substantially 0.1 mm to substantially 2 mm in general. The dendritic cell in the intradermal layer is considered as a cell involved in an antigen-antibody reaction. This is because, when the dendritic cell recognizes the presence of the antigen upon taking in an antigen, an antigen-antibody reaction that activates a lymphocyte having a function of attacking foreign objects is more likely to be induced. Meanwhile, the chromocyte in the intradermal layer has a function of preventing influence of ultraviolet light emitted from an external environment. Further, blood vessels and capillary blood vessels are spread in the dermis on the skin in a complex manner, and sweat glands for adjusting a body temperature, hair roots of body hair (including head hair), and sebaceous glands associated therewith are also present in the dermis. Further, the dermis is a layer between an inside of a human body (the subcutaneous tissue and the muscle tissue) and the epidermis, and includes a fibroblast cell and a collagen cell. Thus, with regard to generation of wrinkles, loss of hair, and the like due to so-called lack of collagen or elastin, a state of the dermis is largely involved.

As described, the human skin structure is formed in a substantially layered manner, and an anatomical function, which is unique to a cell, a tissue, or the like included in each layer, is exerted. This fact indicates that, in a case where medical treatment or the like is performed with respect to the skin, a substance for the treatment is preferably caused to reach a depth of the skin structure body in accordance with a purpose of the treatment. For example, the dendritic cell is present in the intradermal layer, and hence a more effective antigen-antibody reaction can be expected by causing vaccine to reach the layer. Moreover, the chromocyte is present in the intradermal layer, and hence a predetermined substance for skin whitening is also required to be administered in the intradermal layer in a case where so-called beauty treatment for skin whitening is performed. Further, the fibroblast cell and the collagen cell are present in the dermis, and hence a high beauty treatment effect can be expected when proteins, enzymes, vitamins, amino acids, minerals, saccharides, nucleic acids, various growth factors (an epidermic cell and a fibroblast cell), or the like for removing wrinkles of the skin are injected. Moreover, for hair regeneration treatment, a stem cell injection method in which self-culturing a dermal papilla cell, an epidermis stem cell, or the like and self-planting the resultant in head skin or injection of a several kinds of growth factors extracted from a stem cell or nutrient compositions in the vicinity of the dermis are considered to be preferably.

Adjustment of Reached Depth of Injection Solution

The injection solution including the predetermined substance to be administered in accordance with the treatment purpose as described above and the depth of the skin structure body at which the substance is preferably administered correspond to each other individually. In view of this point, the injector 1 is capable of adjusting the reached depth of the injection solution in the target region such as the skin structure body and the like.

Herein, a result obtained by subjecting gel being an artificial target region to an ejection test with the injector 1 is shown below. A distribution state of the injection solution in the gel in the ejection test is schematically illustrated in FIGS. 5A and 5B. FIGS. 5A and 5B schematically illustrate the distribution state of the ejected injection solution in the gel, which was formed over time, from an upper part. Specifically, in FIG. 5A on the top, a first reached depth d1 being a reached depth in the injection solution the gel at the first timing T1 is illustrated. Note that, in the present embodiment, the reached depth of the injection solution is a distance by which the injection solution advanced in the gel along the ejection direction from the injector 1.

Next, in FIG. 5B on the bottom, an on-completion reached depth being a reached depth of the injection solution is indicated with Df with regard to the distribution of the injection solution, which was formed in the gel at the pressurizing completion timing Tf. Moreover, in FIG. 5B on the bottom, an additional reached depth by which the reached depth of the injection solution was increased from the first reached depth d1 illustrated in FIG. 5A on the top to the on-completion reached depth Df is indicated with an additional reached depth d2. Note that, the on-completion reached depth Df indicates a depth by which the injection solution advanced in the gel, which was directly pressurized by combustion of the ignition charge and the gas generating agent 80 in the injector 1, and is strictly different from a diffusion reached depth being a reached depth at which the injection solution was finally diffused over time after ejection in the gel (that is, a reached depth after sufficient time passed from the pressurizing completion timing Tf). However, the diffusion reached depth is formed after the on-completion reached depth Df. Thus, the on-completion reached depth Df is an important element that determines the diffusion reached depth. When the on-completion reached depth Df is adjustable, a sending performance of the injection solution by the injector 1 can be improved drastically.

Herein, the results of the ejection test performed to the gel are shown in Table 1. In the present ejection test, nine patterns were set as combinations of an amount of the ignition charge and an amount of the gas generating agent 80 (mg) set in the injector 1. The first peak pressure P1 (MPa), the first timing T1 (msec), the second peak pressure P2 (MPa), a length between the peaks (msec), the first reached depth d1 (mm), the additional reached depth d2 (mm), and the on-completion reached depth Df (mm) at the time of conducting the ejection test three times for each of the combinations are shown in Table 1. Further, the description of "aa/bb" in the leftmost sections in Table 1 indicate the combinations. Specifically, "aa" indicates the amount of the ignition charge, and "bb" indicates the amount of the gas generating agent 80. Further, the combinations denoted with "*" have different shapes as compared to the combinations of the same amounts without the mark. Note that, the length between the peaks is defined as a difference (T2−T1) between the second timing T2 and the first timing T1.

TABLE 1-continued

|  |  | P1 | T1 | P2 | T2 − T1 | d1 | d2 | Df |
|---|---|---|---|---|---|---|---|---|
| 35/20* | 1 | 8.387 | 1.45 | 12.209 | 11.95 | 4.5 | 2.6 | 7.2 |
|  | 2 | 8.387 | 1.45 | 12.209 | 11.95 | 4.4 | 2.4 | 6.8 |
|  | 3 | 8.387 | 1.45 | 12.209 | 11.95 | 4.2 | 2.4 | 6.6 |
| 35/40* | 1 | 8.560 | 1.50 | 22.370 | 8.05 | 3.9 | 4.8 | 8.8 |
|  | 2 | 8.560 | 1.50 | 22.370 | 8.05 | 5.9 | 3.5 | 9.4 |
|  | 3 | 8.560 | 1.50 | 22.370 | 8.05 | 5.2 | 3.2 | 8.4 |
| 75/0 | 1 | 17.651 | 1.55 | 6.774 | 13.90 | 7.1 | 1.4 | 8.5 |
|  | 2 | 17.651 | 1.55 | 6.774 | 13.90 | 7.2 | 1.6 | 8.8 |
|  | 3 | 17.651 | 1.55 | 6.774 | 13.90 | 8.8 | 1.6 | 10.4 |
| 75/40 | 1 | 20.273 | 1.50 | 25.608 | 13.95 | 8.9 | 2.3 | 11.2 |
|  | 2 | 20.273 | 1.50 | 25.608 | 13.95 | 8.5 | 2.6 | 11.1 |
|  | 3 | 20.273 | 1.50 | 25.608 | 13.95 | 7.0 | 2.5 | 9.5 |
| 110/0 | 1 | 23.326 | 1.55 | 11.188 | 10.25 | 9.3 | 1.4 | 10.7 |
|  | 2 | 23.326 | 1.55 | 11.188 | 10.25 | 9.5 | 1.4 | 10.8 |
|  | 3 | 23.326 | 1.55 | 11.188 | 10.25 | 9.2 | 1.3 | 10.6 |
| 110/40 | 1 | 26.080 | 1.55 | 32.328 | 10.25 | 10.1 | 2.1 | 12.2 |
|  | 2 | 26.080 | 1.55 | 32.328 | 10.25 | 9.2 | 2.0 | 11.2 |
|  | 3 | 26.080 | 1.55 | 32.328 | 10.25 | 9.6 | 2.2 | 11.8 |

Herein, a multiple regression analysis was performed with respect to the first reached depth d1, the additional reached depth d2, and the on-completion reached depth Df being parameters of the reached depth of the injection solution. Specifically, with regard to the first reached depth d1, a multiple regression analysis was performed with two parameters of the first peak pressure P1 and the first timing T1 as explanatory variables. With respect to the additional reached depth d2 and the on-completion reached depth Df, a multiple regression analysis was performed with the first peak pressure P1, the second peak pressure P2, and the length between the peaks (T2−T1) as explanatory variables.

Further, the analysis results relating to the first reached depth d1 are shown in Table 2 and Table 3 given below.

TABLE 2

| Regression statistics | |
|---|---|
| Multiple correlation R | 0.945955 |
| Multiple coefficient of determination R2 | 0.894831 |
| Compensation R2 | 0.886067 |
| Standard error | 0.773946 |
| Observation number | 27 |

TABLE 3

|  | Coefficient | Standard error | t | P-value | Lower limit 95% | Upper limit 95% |
|---|---|---|---|---|---|---|
| Intercept | 13.89445 | 6.505768 | 2.135713 | 0.043109 | 0.467206 | 27.3217 |
| P1 | 0.343321 | 0.030741 | 11.16817 | 5.45E−11 | 0.279874 | 0.406767 |
| T1 | −8.2951 | 4.543428 | −1.82574 | 0.080359 | −17.6723 | 1.082071 |

TABLE 1

|  |  | P1 | T1 | P2 | T2 − T1 | d1 | d2 | Df |
|---|---|---|---|---|---|---|---|---|
| 35/0 | 1 | 8.094 | 1.40 | 2.963 | 21.60 | 6.1 | 1.4 | 7.5 |
|  | 2 | 8.094 | 1.40 | 2.963 | 21.60 | 5.4 | 1.5 | 6.9 |
|  | 3 | 8.094 | 1.40 | 2.963 | 21.60 | 5.0 | 1.8 | 6.8 |
| 35/20 | 1 | 8.494 | 1.50 | 8.494 | 29.60 | 4.5 | 2.5 | 7.0 |
|  | 2 | 8.494 | 1.50 | 8.494 | 29.60 | 4.3 | 2.2 | 6.5 |
|  | 3 | 8.494 | 1.50 | 8.494 | 29.60 | 4.0 | 2.8 | 6.8 |
| 35/40 | 1 | 8.850 | 1.50 | 17.857 | 21.50 | 3.0 | 2.0 | 5.0 |
|  | 2 | 8.850 | 1.50 | 17.857 | 21.50 | 3.5 | 2.1 | 5.5 |
|  | 3 | 8.850 | 1.50 | 17.857 | 21.50 | 4.3 | 3.2 | 7.4 |

From the result that the value of the multiple correlation R is extremely large, it can be understood that the first reached height d1 has a strong correlation with the first peak pressure P1 and the first timing t1. Further, as a trend of the correlation based on the values of t shown in Table 3, there is found a trend that the value of the first reached depth d1 is increased along with increase of the value of the first peak pressure P1 and the value of the first reached depth d1 is increased along with reduction of the value of the first timing T1. The trend indicates that behavior of the injection solution is determined dominantly by the first peak pressure P1 and the first timing T1 at the initial state of the pressure transition shown in FIG. 3.

Next, the analysis results relating to the additional reached depth d2 are shown in Table 4 and Table 5 given below.

TABLE 4

Regression statistics

| Multiple correlation R | 0.833895 |
|---|---|
| Multiple coefficient of determination R2 | 0.695382 |
| Compensation R2 | 0.655649 |
| Standard error | 0.46505 |
| Observation number | 27 |

TABLE 5

| | Coefficient | Standard error | t | P-value | Lower limit 95% | Upper limit 95% |
|---|---|---|---|---|---|---|
| Intercept | 3.073736 | 0.454226 | 6.766977 | 6.68E−07 | 2.134098 | 4.013374 |
| P1 | −0.0969 | 0.015699 | −6.17214 | 2.69E−06 | −0.12937 | −0.06442 |
| P2 | 0.063024 | 0.011829 | 5.327824 | 2.08E−05 | 0.038554 | 0.087495 |
| T2 − T1 | −0.02594 | 0.016483 | −1.57348 | 0.129264 | −0.06003 | 0.008162 |

From the result that the value of the multiple correlation R is extremely large, it can be understood that the additional reached height d2 has a strong correlation with the first peak pressure P1, the second peak pressure P2, and the length between the peaks (T2−T1). Further, as a trend of the correlation based on the values of t shown in Table 5, there is found a trend that the value of the additional reached depth d2 is increase along with reduction of the value of the first peak pressure P1 and the value of the additional reached depth d2 is increased along with increase of the value of the second peak pressure P2. The first peak pressure P1 is a negative factor with respect to the additional reached depth d2 as described above because it is estimated that a force of restoring a local part of the target region, which is deformed around at the first timing T1, to an original state acts largely as the first peak pressure P1 is larger. Note that, based on Table 5 given above, a specific trend between the additional reached depth d2 and the length between the peaks (T2−T1) cannot be found.

Next, the analysis results relating to the on-completion reached depth Df are shown in Table 6 and Table 7 given below.

TABLE 6

Regression statistics

| Multiple correlation R | 0.917731 |
|---|---|
| Multiple coefficient of determination R2 | 0.842231 |
| Compensation R2 | 0.821652 |
| Standard error | 0.873336 |
| Observation number | 27 |

TABLE 7

| | Coefficient | Standard error | t | P-value | Lower limit 95% | Upper limit 95% |
|---|---|---|---|---|---|---|
| Intercept | 6.392808 | 0.853009 | 7.494422 | 1.29E−07 | 4.628225 | 8.157391 |
| P1 | 0.21254 | 0.029482 | 7.20924 | 2.44E−07 | 0.151552 | 0.273527 |
| P2 | 0.018804 | 0.022215 | 0.846478 | 0.406008 | −0.02715 | 0.064759 |
| T2 − T1 | −0.07009 | 0.030954 | −2.26446 | 0.033282 | −0.13413 | −0.00606 |

From the result that the value of the multiple correlation R is extremely large, it can be understood that the on-completion reached depth Df has a strong correlation with the first peak pressure P1, the second peak pressure P2, and the length between the peaks (T2−T1). Further, as a trend of the correlation based on the values of t shown in Table 7, there is found a trend that the value of the on-completion reached depth Df is increased along with increase of the value of the first peak pressure, the value of the on-completion reached depth Df is increased along with increase of the value of the second peak pressure P2, and the value of the on-completion reached depth Df is increased along with reduction of the value of the length between the peaks (T2−T1). The length between the peaks (T2−T1) is a negative factor with respect to the on-completion reached depth Df as described above because it is estimated that a time required for restoring the local part of the target region, which is deformed around at the first timing T1, to an original state becomes shorter as the length between the peaks (T2−T1) becomes smaller. Note that, it can be understood that the strength of the correlation between the second peak pressure P2 and the on-completion reached depth Df is relatively smaller than the strength of the correlation between the first peak pressure P1 and the on-completion reached depth Df and the strength of the correlation between the length between the peaks (T2−T1) and the on-completion reached depth Df.

Herein, as described above, it is important to adjust the on-completion reached depth Df accurately when the reached depth of the injection solution in the target region is adjusted. In view of this, in consideration of the above-mentioned analysis results relating to the on-completion reached depth Df, it has been found out that, first, focusing on both the parameters being the first peak pressure P1 and the length between the peaks (T2−T1) is effective. In view of this, with the injector 1, the on-completion reached depth Df is larger along with increase of the first peak pressure P1, and the on-completion reached depth Df is larger along with reduction of the length between the peaks (T2−T1). In view of this, a kind, an amount, a shape, and the like of the ignition charge and the gas generating agent 80 mounted in the injector 1 are designed, and thus the transition of the ejection pressure of the injection solution from the injector 1, which achieves the desired on-completion reached depth Df, is achieved.

The limited ejection parameters being the first peak pressure P1 and the length between the peaks (T2−T1) included in the transition of the ejection pressure of the injection solution are used as described above. With this, the on-completion reached depth Df of the injector 1 can be adjusted in an extremely satisfactory manner. With this, injection with the injector 1 can be effective, and an adjustment burden that a user bears to obtain the effect can be drastically alleviated. That is, a technical idea of adjusting the limited parameters in the injector 1 as described above can exert an extremely advantageous effect of achieving both an injection effect of the injector 1 and alleviation of the adjustment burden for the effect in a compatible manner.

Next, it is advantageous to preferably focus on the second peak pressure P2 having a correlation with the on-completion reached depth Df. As described above, the strength of the correlation between the second peak pressure P2 and the on-completion reached depth Df is smaller than the first peak pressure P1 and the length between the peaks (T2−T1). Still, it is at least a parameter having a correlation with the completion reached depth Df. Therefore, in addition to the first peak pressure P1 and the length between the peaks (T2−T1), the on-completion reached depth Df is further adjusted with the second peak pressure P2, and thus the adjustment accuracy can be improved. In view of this, with the injector 1, the on-completion reached depth Df is larger along with increase of the first peak pressure P1, the on-completion reached depth Df is larger along with reduction of the length between the peaks (T2−T1), and further the on-completion reached depth Df is larger along with increase of the second peak pressure. In view of this, a kind, an amount, a shape, and the like of the ignition charge and the gas generating agent 80 mounted in the injector 1 are designed, and thus the transition of the ejection pressure of the injection solution from the injector 1, which achieves the desired on-completion reached depth Df, is achieved. Also in this case, the parameters for adjusting the on-completion reached depth Df are limited to the second peak pressure P2 in addition to the first peak pressure P1 and the length between the peaks (T2−T1). Thus, similarly to the case described above, both an injection effect of the injector 1 and alleviation of the adjustment burden for the effect can be achieved in a compatible manner.

Moreover, when the additional reached depth d2 is adjusted accurately, as a result, it is considered that the on-completion reached depth Df can be adjusted more accurately. This is because the additional reached depth d2 is defined as a depth from the first reached depth d1 to the on-completion reached depth Df, and a step of forming the additional reached depth d2, so to speak, can be considered as a step of enabling fine adjustment of the on-completion reached depth Df in the latter half process of the ejection pressure transition (the process after the first timing T1). In view of this, in consideration of the analysis results relating to the additional reached depth d2 shown in Table 4 and Table 5 given above, it has been found out that further focusing on both the parameters being the first peak pressure P1 and the second peak pressure P2 is effective. With the injector 1, the additional reached depth d2 is larger along with increase of the second peak pressure P2, and the additional reached depth d2 is larger along with reduction of the first peak pressure P1. In view of this, as a result, a kind, an amount, a shape, and the like of the ignition charge and the gas generating agent 80 mounted in the injector 1 are designed, and thus the transition of the ejection pressure of the injection solution from the injector 1, which achieves the desired on-completion reached depth Df, is achieved. By adjusting the correlation of the first peak pressure P1 and the correlation of the second peak pressure P2, the on-completion reached depth Df can be adjusted more accurately through adjustment of the additional reached depth d2.

Note that, the first reached depth d1 itself is a parameter indicating behavior of the injection solution at the initial stage of the ejection pressure transition. Thus, for the purpose of adjusting the on-completion reached depth Df accurately, the analysis results relating to the first reached depth d1 shown in Table 2 and Table 3 given above are not required to be considered. However, this does not exclude adjustment of the on-completion reached depth Df by further using the analysis results relating to the first reached depth d1.

First Adjustment Method for Reached Depth of Injector 1

Figure 6:
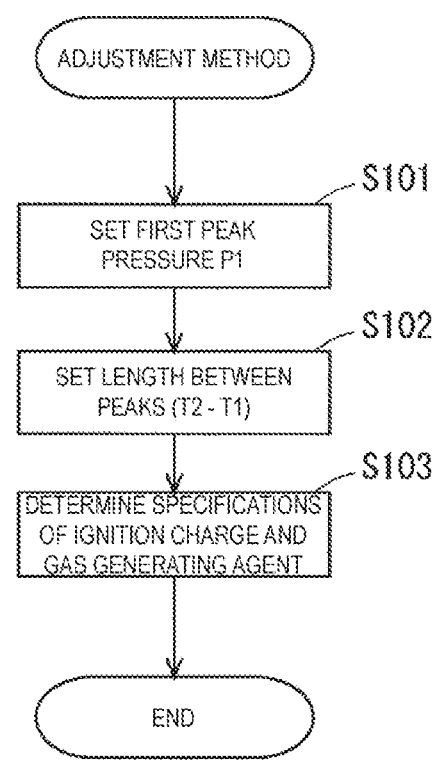
FIG. 6 is a first flowchart relating to a method of adjusting a pressurizing mode of an injector according to an embodiment of the present invention, the injector sending an injection solution into a desired reached depth in a target region.

In consideration of the relationships between the on-completion reached depth Df and the respective ejection parameters relating to the ejection pressure transition in the injector 1 described above, a first adjustment method for the on-completion reached depth Df of the injector 1 is described with reference to FIG. 6. The adjustment method illustrated in FIG. 6 is an adjustment method for the on-completion reached depth Df based on the first peak pressure P1 and the length between the peaks (T2−T1) as described above. First, in S101, in accordance with a first adjustment reference that the on-completion reached depth Df is increased along with increase of the first peak pressure P1, the first peak pressure P1 for achieving the desired on-completion reached depth Df is set. Specifically, in consideration of the coefficient sections of the analysis results in Table 7, the on-completion reached depth Df can be expressed in Regression Equation 1 given below.

$$Df = 6.39 + 0.21 \times P1 - 0.07 \times (T2-T1) \qquad \text{Equation 1}$$

The part "+0.21×P1" in Equation 1 corresponds to the above-mentioned first adjustment reference. Herein, the first peak pressure P1 is set in consideration of the fact that the ejected injection solution is required to penetrate the surface of the target region at the initial stage of ejection of the injection solution. This indicates that a lower limit value P1 min is set as the value of the first peak pressure P1 for ensuring the surface penetration. In view of this, in S101, the first peak pressure P1 being a value equal to or more than the lower limit value P1 min is set.

Subsequently, in S102, in accordance with a second adjustment reference that the on-completion reached depth Df is increased along with reduction of the length between the peaks (T2−T1), the length between the peaks (T2−T1) for achieving the desired on-completion reached depth Df is set. The part "−0.07×(T2−T1)" in Equation 1 given above corresponds to the above-mentioned second adjustment reference. Herein, when the length between the peaks (T2−T1) is set, it is required to consider the combustion speed of the gas generating agent 80. This is because the combustion speed of the gas generating agent 80 is relatively lower than that of the ignition charge, and it is difficult to physically reduce the speed to a value less than a predetermined threshold value. This indicates that a lower limit value ΔTmin is set as the length between the peaks (T2−T1). In view of this, in S101, the length between the peaks (T2−T1) being a value equal to or more than the lower limit value ΔTmin is set.

Note that, in the above-mentioned embodiment, setting of the first peak pressure P1 and setting of the length between the peaks (T2−T1) are performed in the stated order. However, the order of the setting processing is not limited thereto. That is, the length between the peaks (T2−T1) may be set prior to the first peak pressure P1. Alternatively, setting of the first peak pressure P1 and setting of the length between the peaks (T2−T1) may be set substantially at the same time. The important point is that each of the first peak pressure P1 and the length between the peaks (T2−T1) is set in accordance with Regression Equation 1 given above.

Figure 7A:
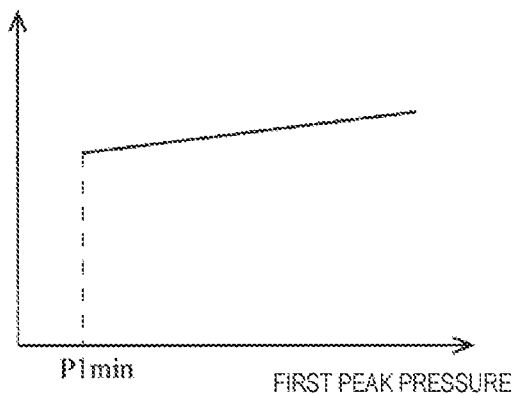
FIG. 7A is a view illustrating a relationship between a first peak pressure and an ignition charge amount and a relationship between a length between peaks and a gas generating agent amount, which are used in the adjustment method illustrated in FIG. 6.
Figure 7B:
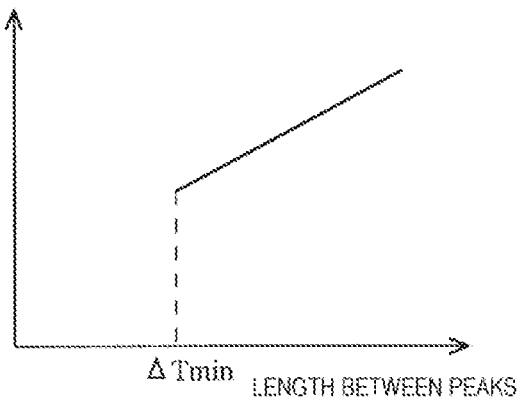
FIG. 7B is a view illustrating a relationship between a first peak pressure and an ignition charge amount and a relationship between a length between peaks and a gas generating agent amount, which are used in the adjustment method illustrated in FIG. 6.

After setting of the first peak pressure P1 and setting of the length between the peaks (T2−T1) are performed, the amount of the ignition charge and the amount of the gas generating agent 80, which are specifications relating to pressurizing of the injection solution, are determined in S103, and thus those values of the ejection parameters are reflected on the actual ejection pressure transition. Specifically, the ignition charge amount is determined based on the correlation between the first peak pressure P1 and the ignition charge amount shown in the FIG. 7A on the top. The correlation has a relationship that the ignition charge amount is increased along with increase of the first peak pressure P1. Further, the gas generating agent amount is determined based on the correlation between the length between the peaks (T2−T1) and the gas generating agent amount shown in FIG. 7B on the bottom. In consideration of the fact that the combustion speed of the gas generating agent 80 is lower than the combustion speed of the ignition charge, the correlation has a relationship that the gas generating agent amount is increased along with increase of the length between the peaks (T2−T1). Further, by comparing 35/20 and 35/20* or comparing 35/40 and 35/40* in the combinations of the ignition charge and the amount of the gas generating agent 80 in Table 1 given above, it can be understood that a difference in the shape of the gas generating agent 80 is a parameter that may adjust the length between the peaks. In view of this, the length between the peaks (T2−T1) may be adjusted by changing the shape of the gas generating agent 80.

The ignition charge and the amount of the gas generating agent 80 are determined by the adjustment method illustrated in FIG. 6 as described above. With this, at the time of operating the injector 1, the ejection pressure transition including the set first peak pressure P1 and the set length between the peaks (T2−T1) can be formed. With this, the on-completion reached depth Df of the injection solution in the target region can be adjusted to a desired value.

Second Adjustment Method for Reached Depth of Injector 1

Figure 8:
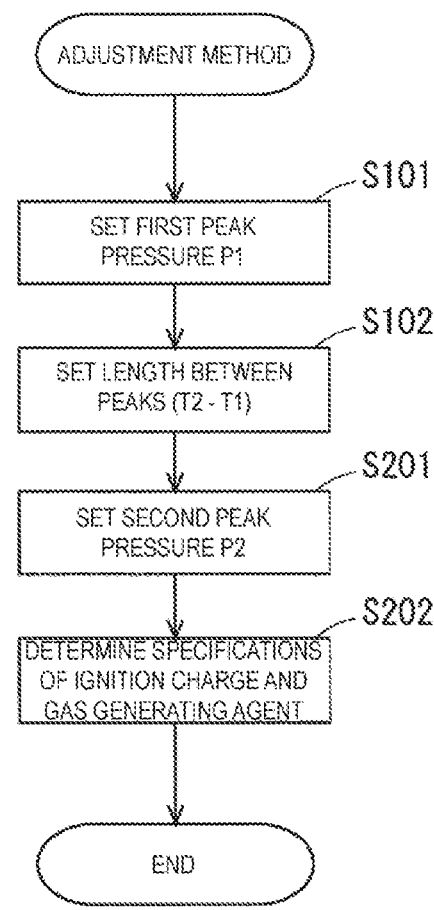
FIG. 8 is a second flowchart relating to a method of adjusting a pressurizing mode of an injector according to an embodiment of the present invention, the injector sending an injection solution into a desired reached depth in a target region.

In consideration of the relationships between the on-completion reached depth Df and the respective ejection parameters relating to the ejection pressure transition in the injector 1 described above, a second adjustment method for the on-completion reached depth Df of the injector 1 is described with reference to FIG. 8. The adjustment method illustrated in FIG. 8 is an adjustment method for the on-completion reached depth Df based on the second peak pressure P2 in addition to the first peak pressure P1 and the length between the peaks (T2−T1) as described above. Note that, the processing contents in S101 and S102 in FIG. 8 are substantially the same as the processing denoted with the same reference numerals in FIG. 6, and hence detailed description thereof is omitted. However, in the second adjustment method, in consideration of the coefficient sections of the analysis results in Table 7, the on-completion reached depth Df can be expressed in Regression Equation 2 given below.

$$Df = 6.39 + 0.21 \times P1 + 0.02 \times P2 - 0.07 \times (T2-T1) \quad \text{Equation 2}$$

Further, the part "+0.21×P1" in Equation 1 corresponds to the first adjustment reference in the second adjustment method, and the part "−0.07×(T2−T1)" corresponds to the second adjustment reference in the second adjustment method.

Further, after S102 is completed, the processing in S201 is performed. In S201, in accordance with a third adjustment reference that the on-completion reached depth Df is increased along with increase of the second peak pressure P2, the second peak pressure P2 for achieving the desired on-completion reached depth Df is set. The part "+0.02×P2" in Equation 2 given above corresponds to the above-mentioned third adjustment reference. Herein, when the second peak pressure P2 is set, it is required to consider the length between the peaks (T2−T1) set in S102. This is because the length between the peaks (T2−T1) has a correlation with the amount of the gas generating agent 80 and the second peak pressure P2 also has a correlation with the amount of the gas generating agent 80. In view of this, in a case where the second peak pressure P2 is set in S201, the desired on-completion reached depth Df is achieved in consideration of the balance with the length between the peaks set in S102.

After setting of the first peak pressure P1, setting of the length between the peaks (T2−T1), and setting of the second peak pressure P2 are performed, the amount of the ignition charge and the amount of the gas generating agent 80, which are specifications relating to pressurizing of the injection solution, are determined in S202, and thus those values of the ejection parameters are reflected on the actual ejection pressure transition. Determination of the amount of the ignition charge in the processing in S202 is basically the same as the case of the processing in S103 included in the adjustment method in FIG. 6. As described above, the amount of the gas generating agent 80 has a correlation with both the length between the peaks (T2−T1) and the second peak pressure P2. Thus, in place of the correlation between the gas generating agent amount and the length between the peaks shown in the FIG. 7B on the bottom, the amount of the gas generating agent 80 is determined in consideration of the correlation between the gas generating agent amount and both the length between the peaks (T2−T1) and the second peak pressure P2. The correlation has a relationship that the gas generating agent amount is increased along with increase of the length between the peaks (T2−T1) and increase of the second peak pressure P2.

The ignition charge and the amount of the gas generating agent 80 are determined by the adjustment method illustrated in FIG. 8 as described above. With this, at the time of operating the injector 1, the ejection pressure transition including the set first peak pressure P1, the second peak pressure P2, and the set length between the peaks (T2−T1) can be formed. With this, the on-completion reached depth Df of the injection solution in the target region can be adjusted to a desired value.

Third Adjustment Method for Reached Depth of Injector 1

Figure 9:
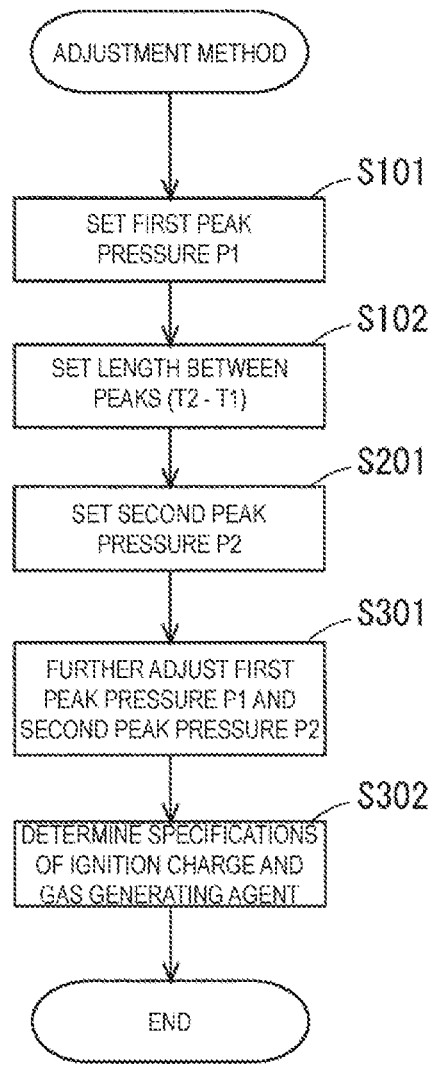
FIG. 9 is a third flowchart relating to a method of adjusting a pressurizing mode of an injector according to an embodiment of the present invention, the injector sending an injection solution into a desired reached depth in a target region.

In consideration of the relationships between the additional reached depth d2 and the respective ejection parameters in addition to the relationships between the on-completion reached depth Df and the respective ejection parameters relating to the ejection pressure transition in the injector 1 described above, a third adjustment method for the on-completion reached depth Df of the injector 1 is described with reference to FIG. 9. The processing contents in S101 and S102 and the processing content in S201 in the adjustment method in FIG. 9 are substantially the same as the processing denoted with the same reference numerals in FIGS. 7A and 7B, and hence detailed description thereof is omitted.

Further, after S201 is completed, the processing in S301 is performed. In S301, in accordance with a fourth adjustment reference that the additional reached depth d2 is increased along with increase of the second peak pressure P2 and reduction of the first peak pressure P1, the first peak pressure P1 and the second peak pressure P2 are further adjusted. Note that, in the third adjustment method, in consideration of the coefficient sections of the analysis results in Table 5, the additional reached depth d2 can be expressed in Regression Equation 3 given below.

$$d2=3.07-0.10\times P1+0.06\times P2 \qquad \text{Equation 3}$$

Further, the part "$-0.10\times P1+0.06\times P2$" in Equation 3 corresponds to the fourth adjustment reference. Herein, adjustment of the first peak pressure P1 and the second peak pressure P2 in S301 is performed for the purpose of eliminating an error that may be included in the on-completion reached depth Df that is estimated based on each of the pressure values set in S101 and S201. Therefore, independently from S101 and S201, in other words, from aspects different from the processing in S101 and S201, the values of the first peak pressure P1 and the second peak pressure P2 are recalculated in the processing in S301. For example, an allowable range of the additional reached depth d2 is set in advance. In a case where, with each of the pressure values set in S101 and S201, the additional reached depth d2 does not fall within the allowable range, adjustment of the first peak pressure P1 and the second peak pressure P2 is performed, and thus the additional reached depth d2 falls within the allowable range.

After adjustment of the first peak pressure P1 and the second peak pressure P2 is performed, the amount of the ignition charge and the amount of the gas generating agent 80, which are specifications relating to pressurizing of the injection solution, are determined in S302, and thus those values of the ejection parameters are reflected on the actual ejection pressure transition. The processing content in S302 is substantially the same as the processing content in S202 in FIG. 8, and hence detailed description thereof is omitted.

The ignition charge and the amount of the gas generating agent 80 are determined by the adjustment method illustrated in FIG. 9 as described above. With this, at the time of operating the injector 1, the ejection pressure transition including the set first peak pressure P1, the second peak pressure P2, and the set length between the peaks (T2–T1) can be formed. With this, the on-completion reached depth Df of the injection solution in the target region can be adjusted to a desired value.

Processing Device for Adjustment for Reached Depth of Injector 1 and Program

Figure 10:
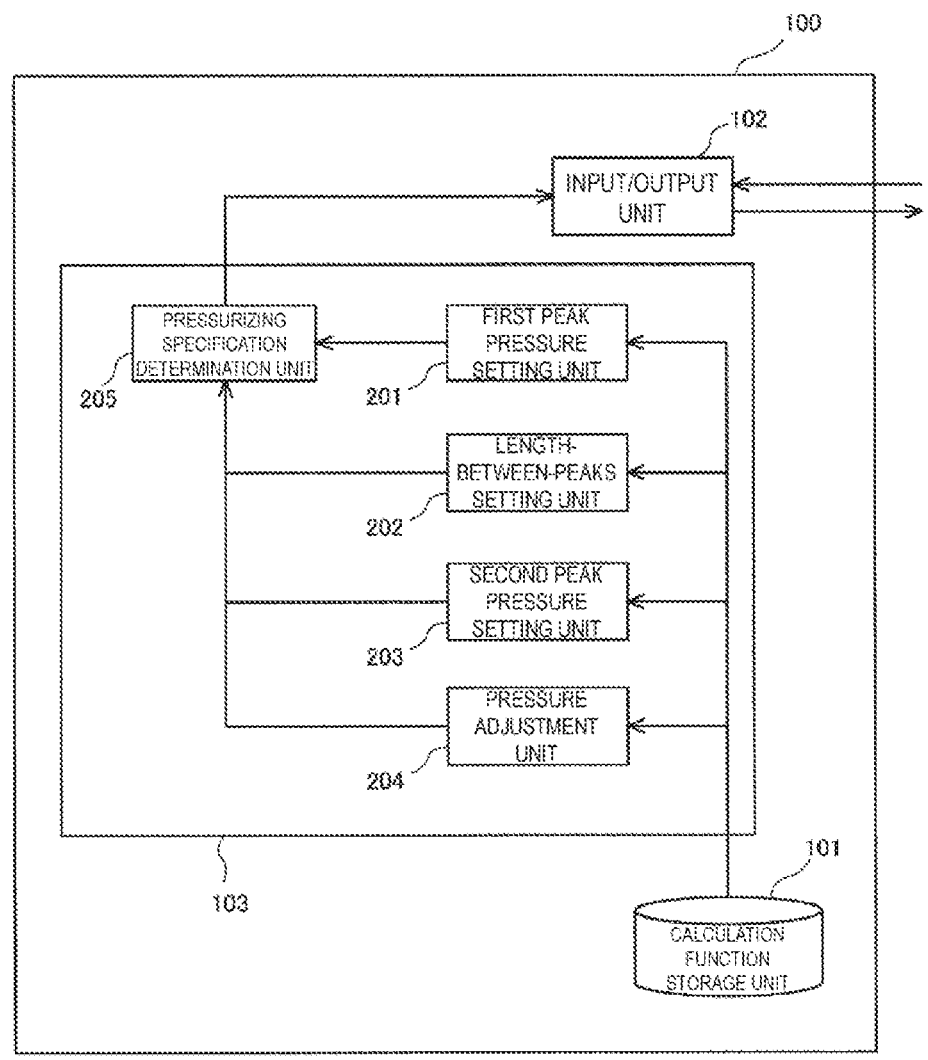
FIG. 10 is a function block diagram of a processing device that achieves an adjustment method of an injector according to an embodiment of the present invention.

Now, with reference to FIG. 10, a processing device 100 that executes the adjustment methods illustrated in FIG. 6, FIG. 8, and FIG. 9 and a program that causes the processing device 100 to execute those adjustment methods are described. FIG. 10 is a view obtained by visualizing functional units formed in the processing device 100 for achieving the processing relating to the adjustment method. In the processing device 100, the functional units illustrated in FIG. 10 are formed by executing a predetermined program through use of an arithmetic unit, a memory, and the like therein, and thus each of the adjustment methods described above is achieved.

Now, the functional units of the processing device 100 are described. The processing device 100 includes a calculation function storage unit 101, an input/output unit 102, and an arithmetic unit 103. The calculation function storage unit 101 is a functional unit that stores the functions for calculating the on-completion reached depth Df and the additional reached depth d2, specifically, the functions expressed with Equation 1 to Equation 3 given above in the adjustment methods in FIG. 6, FIG. 8, and FIG. 9. The stored information on the functions is used in, for example, the setting processing for the first peak pressure and the like as in the adjustment method described above. The input/output unit 102 is a functional unit that inputs request information from a user, which relates to determination of the pressurizing specifications of the injector 1 (the amount of the ignition charge and the amount of the gas generating agent) and outputs, to the user, the information on the pressurizing specifications calculated by the processing device 100. The input request information is input through an input device (a keyboard, a mouse, or the like) included in the processing device 100, or is input from a device different from the processing device 100 via a predetermined interface. Further, outputting of the information on the determined pressurizing specifications may include a mode of displaying the information on a display device (display) of the processing device 100 and a mode of transmitting the information as electronic information to another processing device in a case where the information on the pressurizing specifications is used in the other device.

The arithmetic unit 103 is a functional unit that performs setting and adjustment of the ejection parameters being the first peak pressure P1, the second peak pressure P2, and the length between the peaks (T2–T1) in the adjustment method described above for achieving the desired on-completion reached depth Df and performs determination of the amount of the ignition charge and the amount of the gas generating agent being the pressurizing specifications based on the ejection parameters. Specifically, the arithmetic unit 103 includes a first peak pressure setting unit 201, a length-between-the-peaks setting unit 202, a second peak pressure setting unit 203, a pressure value adjustment unit 204, and a pressurizing specifications determination unit 205 as subfunctional units. The first peak pressure setting unit 201 is a functional unit that sets the first peak pressure P1 for achieving the desired on-completion reached depth Df, and specifically executes the processing in S101 in the adjustment method described above. The length-between-the-peaks setting unit 202 is a functional unit that sets the length between the peaks (T2–T1) for achieving the desired on-completion reached depth Df, and specifically executes the processing in S102 in the adjustment method described above. The second peak pressure setting unit 203 is a functional unit that sets the second peak pressure P2 for achieving the desired on-completion reached depth Df, and specifically executes the processing in S201 in the adjustment method described above. The pressure value adjustment unit 204 is a functional unit that adjusts the value of the first peak pressure P1 and the value of the second peak pressure P2 set by the first peak pressure setting unit 201 and the second peak pressure setting unit 203 for achieving the desired on-completion reached depth Df, and specifically executes the processing in S301 in the adjustment method described above. Finally, the pressurizing specifications determination unit 205 is a functional unit that determines the amount of the ignition charge and the amount of the gas generating agent being the pressurizing specifications in the injector 1 for enabling the values of the ejection parameters obtained in the processing by the setting units and the pressure value adjustment unit to be reflected on the actual ejection pressure transition, and specifically executes the processing in S103, S202, and S302 in the adjustment method described above.

By configuring the processing device 100 as described above or installing a program for forming the respective functional units in the processing device 100, the adjustment methods in FIG. 6, FIG. 8, and FIG. 9 are achieved with the processing device 100. As a result, a user can obtain the information on the pressurizing specifications of the injector 1 more easily, and hence can cause the injection solution to reach the desired depth in the target region with the injector 1.

Modified Example 1

As a further modified example of the injector 1, for example, there can be exemplified a device that performs inoculation with a cultured cell, a stem cell, or the like into a cell, a scaffold tissue, or a scaffold being an injection target in a field of regenerative medicine for a human. For example, as described in JP 2008-206477 A, in accordance with an implanted part and a purpose of re-cellularization, a cell that can be determined appropriately by a person skilled in the art, for example, an endothelial cell, an endothelial precursor cell, a myeloid cell, a preosteoblast cell, a cartilagenous cell, a fibroblast cell, a skin cell, a muscle cell, a liver cell, a kidney cell, an intestinal cell, a stem cell, or any other cells that may be considered in a field of regenerative medicine is administered.

Moreover, the injector 1 may be configured as an injector that sends DNA or the like into a cell, a scaffold tissue, a scaffold, or the like as described in Japanese Translation of PCT International Application Publication No. 2007-525192. Moreover, the injector 1 may be configured as an injector that directly sends various genes, a cancer-suppressing cell, a lipid envelope, or the like into a target tissue or administers an antigenic gene for enhancing immunity against a pathogen, or an injector applicable to a field of treatment for various diseases (the fields described in Japanese Translation of PCT International Application Publication No. 2008-508881, Japanese Translation of PCT International Application Publication No. 2010-503616, and the like), a field of immunological medicine (the field described in Japanese Translation of PCT International Application Publication No. 2005-523679 and the like), and the like.

Modified Example 2

The technical idea disclosed in relation to the injector 1 according to the present invention is also applicable to an injector that performs pressurizing of the injection solution in a mode other than combustion of the ignition charge and the gas generating agent. For example, in a case of an injector capable of forming the ejection pressure transition as shown in FIG. 3 by performing pressurizing of the injection solution through use of an energy of a spring, compressed gas, or the like, the injection solution can be caused to reach the desired depth in the target region by adopting the adjustment method described above. Further, even in a case where an injector uses the ignition charge for generating the first peak pressure and compressed gas for generating the second peak pressure and forms the ejection pressure transition as shown in FIG. 3, the adjustment method described above can be adopted, and the injection solution can be caused to reach the desired depth in the target region. Further, even in a case where an injector uses the ignition charge for generating the first peak pressure and an elastic energy of an elastic member such as a spring for generating the second peak pressure and forms the ejection pressure transition as shown in FIG. 3, the adjustment method described above can be adopted, and the injection solution can be caused to reach the desired depth in the target region.

REFERENCE SIGNS LIST

1 Injector
2 Housing
3 Syringe portion
4 Plunger
5 Piston
6 Injector body
7 Drive portion
8 Button
9 Battery
10 Device assembly
10A, 10B Sub-assembly
31 Nozzle portion
32 Filling chamber
44 Rod portion
53 Pressing pillar portion
54 Accommodation hole
64 Through-hole
71 Igniter
80 Gas generating agent
100 Processing device

What is claimed is:

1. A needleless injector that injects a substance to be injected to a target region without using an injection needle, the needleless injector comprising:

an encapsulating portion configured to encapsulate the substance to be injected;
a pressurizing portion configured to pressurize the substance encapsulated in the encapsulating portion; and
a flow path including an ejection port through which the substance pressurized by the pressurizing portion is ejected to the target region,
wherein:
the pressurizing portion is configured to pressurize the substance having an ejection pressure defined as a pressure of the substance ejected through the ejection port, the ejection pressure being raised to a first peak pressure after pressurizing is started, being lowered to a pressure lower than the first peak pressure afterward, and then being raised to a second peak pressure again, and
an on-completion reached depth that is an on-completion reached depth of the substance in the target region when the pressurizing portion completes pressurizing at a pressurizing completion timing when the ejection pressure is substantially zero is adjustable, the on-completion reached depth configured to increase along with an increase of the first peak pressure in combination with reduction of a length between peaks from a first timing at which the ejection pressure reaches the first peak pressure to a second timing at which the ejection pressure reaches the second peak pressure.

2. The needleless injector according to claim 1, wherein the on-completion reached depth of the substance in the target region is further adjustable, the on-completion reached depth being increased along with an increase of the second peak pressure.

3. The needleless injector according to claim 2, wherein the on-completion reached depth is further adjustable by adjusting an additional reached depth from a reached depth of the substance at the first timing in the target region to the on-completion reached depth, the additional reached depth being increased along with an increase of the second peak pressure and being increased along with reduction of the first peak pressure.

4. The needleless injector according to claim 1, further comprising:
an igniter including an ignition charge; and
a gas generating agent that is disposed in a combustion chamber into which a combustion product generated by combustion of the ignition charge flows and that is configured to be combusted by the combustion product and to generate predetermined gas,
wherein:
the ignition charge comprises any one of an explosive containing zirconium and potassium perchlorate, an explosive containing titanium hydride and potassium perchlorate, an explosive containing titanium and potassium perchlorate, an explosive containing aluminum and potassium perchlorate, an explosive containing aluminum and bismuth oxide, an explosive containing aluminum and molybdenum oxide, an explosive containing aluminum and copper oxide, an explosive containing aluminum and iron oxide, or an explosive including a combination of a plurality of the explosives,
the gas generating agent is configured to be formed to be combusted at a combustion speed lower than a combustion speed of the ignition charge, and
the pressurizing portion is configured to cause the ejection pressure of the substance to reach the first peak pressure with a combustion pressure of the ignition charge by operating the igniter, and cause the ejection pressure of the substance to reach the second peak pressure with a combustion pressure of the gas generating agent that is configured to be combusted subsequent to the ignition charge.

5. An adjustment method of adjusting an on-completion reached depth with a needleless injector, the adjustment method of adjusting the on-completion reached depth of a substance to be injected in a target region when pressurizing is completed at a pressurizing completion timing when an ejection pressure is substantially zero being performed with the needleless injector configured to inject the substance to the target region without using an injection needle by pressurizing the substance that is encapsulated and ejecting the substance that is pressurized through an ejection port to the target region,
the needleless injector being configured to pressurize the substance having the ejection pressure defined as a pressure of the substance ejected through the ejection port, the ejection pressure being raised to a first peak pressure after pressurizing is started, being lowered to a pressure lower than the first peak pressure afterward, and then being raised to a second peak pressure again,
the adjustment method comprising:
setting the first peak pressure in accordance with a first adjustment reference and setting a length between peaks in accordance with a second adjustment reference that the on-completion reached depth is increased along with an increase of the first peak pressure in combination with reduction of the length between the peaks required from a first timing at which the ejection pressure reaches the first peak pressure to a second timing at which the ejection pressure reaches the second peak pressure; and
determining predetermined pressurizing specifications relating to pressurizing of the substance, based on the first peak pressure and the length between the peaks that are set.

6. The adjustment method of adjusting an on-completion reached depth with a needleless injector according to claim 5, further comprising setting the second peak pressure in accordance with a third adjustment reference that the on-completion reached depth is increased along with an increase of the second peak pressure, wherein:
during the determining of the predetermined pressurizing specifications, the predetermined pressurizing specifications are determined based on the second peak pressure that is set, in addition to the first peak pressure and the length between the peaks that are set.

7. The adjustment method of adjusting an on-completion reached depth with a needleless injector according to claim 6, further comprising further adjusting the first peak pressure and the second peak pressure in accordance with a fourth adjustment reference that an additional reached depth from a reached depth of the substance at the first timing in the target region to the on-completion reached depth is increased along with an increase of the second peak pressure and is increased along with reduction of the first peak pressure, wherein
during the determining of the predetermined pressurizing specifications, the predetermined pressurizing specifications are determined based on the first peak pressure and the second peak pressure that are further adjusted and the length between the peaks.

8. A non-transitory computer-readable recording medium storing therein an ejection parameter calculation program for a needleless injector, the program causing a processing device to calculate predetermined ejection parameters for the needleless injector for adjusting an on-completion reach depth of a substance to be injected in a target region when pressurizing is completed at a pressurizing completion timing when an ejection pressure is substantially zero, which is performed with the needleless injector configured to inject the substance to the target region without using an injection needle by pressurizing the substance that is encapsulated and ejecting the substance that is pressurized through an ejection port to the target region,
the needleless injector being configured to pressurize the substance having ft the ejection pressure defined as a pressure of the substance ejected through the ejection port, the ejection pressure being raised to a first peak pressure after pressurizing is started, being lowered to a pressure lower than the first peak pressure afterward, and then being raised to a second peak pressure again,
the program causing the processing device to execute:
calculating the first peak pressure in accordance with a first adjustment reference and calculating a length between peaks in accordance with a second adjustment reference that the on-completion reached depth is increased along with an increase of the first peak pressure in combination with reduction of the length between the peaks required from a first timing at which the ejection pressure reaches the first peak pressure to a second timing at which the ejection pressure reaches the second peak pressure; and
determining predetermined pressurizing specifications relating to pressurizing of the substance, based on the first peak pressure and the length between the peaks that are set.

9. The non-transitory computer-readable recording medium according to claim 8, the program further causing the processing device to execute calculating the second peak pressure in accordance with a third adjustment reference that the on-completion reached depth is increased along with an increase of the second peak pressure, wherein:

during the determining of the predetermined pressurizing specifications, the processing device is caused to determine the predetermined pressurizing specifications, based on the second peak pressure that is set, in addition to the first peak pressure and the length between the peaks that are set.

10. The non-transitory computer-readable recording medium according to claim 9, the program further causing the processing device to execute adjusting the first peak pressure and the second peak pressure in accordance with a fourth adjustment reference that an additional reached depth from a reached depth of the substance at the first timing in the target region to the on-completion reached depth is increased along with an increase of the second peak pressure and is increased along with reduction of the first peak pressure, wherein:

during the determining of the predetermined pressurizing specifications, the processing device is caused to determine the predetermined pressurizing specifications, based on the first peak pressure and the second peak pressure that are further adjusted and the length between the peaks.

11. The needleless injector according to claim 1, wherein the on-completion reached depth is expressed by the following equation:

$$Df = c1 + c2 \times P1 - c3 \times (T2 - T1),$$

where Df is the on-completion reached depth, P1 is the first peak pressure, T1 is the first timing, T2 is the second timing, and c1, c2, and c3 are non-zero coefficients.

12. The needleless injector according to claim 2, wherein on-completion reached depth is expressed by the following equation:

$$Df = c1 + c2 \times P1 + c4 \times P2 - c3 \times (T2 - T1),$$

where Df is the on-completion reached depth, P1 is the first peak pressure, P2 is the second peak pressure, T1 is the first timing, T2 is the second timing, and c1, c2, c3, and c4 are non-zero coefficients.

13. The needleless injector according to claim 1, wherein T2−T1 is greater than Tf−T2, where T1 is the first timing, T2 is the second timing, and Tf is the pressurizing completion timing.

* * * * *